(12) United States Patent
Foley et al.

(10) Patent No.: US 12,084,543 B2
(45) Date of Patent: Sep. 10, 2024

(54) POLYETHER DERIVATIVES, USES, AND METHODS OF MAKING THE SAME

(71) Applicant: P2 Science, Inc., Woodbridge, CT (US)

(72) Inventors: Patrick Foley, New Haven, CT (US); Tania Salam, New Haven, CT (US); Anam Ikram, Woodbridge, CT (US)

(73) Assignee: P2 SCIENCE, INC., Woodbridge, CT (US)

( * ) Notice: Subject to any disclaimer, the term of this patent is extended or adjusted under 35 U.S.C. 154(b) by 1026 days.

(21) Appl. No.: 16/978,076

(22) PCT Filed: Mar. 7, 2019

(86) PCT No.: PCT/US2019/021187
§ 371 (c)(1),
(2) Date: Sep. 3, 2020

(87) PCT Pub. No.: WO2019/173614
PCT Pub. Date: Sep. 12, 2019

(65) Prior Publication Data
US 2020/0392287 A1    Dec. 17, 2020

Related U.S. Application Data

(60) Provisional application No. 62/639,784, filed on Mar. 7, 2018.

(51) Int. Cl.
C08G 65/34     (2006.01)
(52) U.S. Cl.
CPC .................................. C08G 65/34 (2013.01)

(58) Field of Classification Search
CPC . C08G 65/34; C08G 2/24; C08G 2/10; C08G 4/00
See application file for complete search history.

(56) References Cited

U.S. PATENT DOCUMENTS

| | | |
|---|---|---|
| 2,020,298 A | 11/1935 | Carothers et al. |
| 3,829,505 A | 8/1974 | Johnston |
| 3,980,697 A | 9/1976 | El-Chahawi et al. |
| 4,021,507 A | 5/1977 | Ford |
| 4,218,379 A | 8/1980 | Harris et al. |
| 4,366,270 A | 12/1982 | Ruter |
| 4,381,416 A | 4/1983 | Kyo et al. |
| 5,030,768 A | 7/1991 | Chen et al. |
| 5,264,547 A | 11/1993 | Yamaguchi et al. |

(Continued)

FOREIGN PATENT DOCUMENTS

| | | | |
|---|---|---|---|
| DE | 10 2005 025 739 A1 | 12/2006 | |
| EP | 0841333 A1 | 5/1998 | |

(Continued)

OTHER PUBLICATIONS

Swift et al., "Catalytic Transformations of the Major Terpene Feedstocks", *Topics in Catalysis*, 27(1-4), pp. 143-155, (2004).

(Continued)

*Primary Examiner* — Shane Fang
(74) *Attorney, Agent, or Firm* — Hoxie & Associates LLC

(57) ABSTRACT

The present disclosure is directed to certain polyethers copolymers, and polyether derivatives thereof, and methods of making and using the same. For example, the starting materials may include such species as citronellol, geraniol, dihydromyrcene, adipic acid, propanediol, ethylene glycol, glycerol, 1,9-nonanediol, and 1,6-hexanediol.

21 Claims, 6 Drawing Sheets

(56) References Cited

U.S. PATENT DOCUMENTS

| | | | |
|---|---|---|---|
| 5,292,845 | A | 3/1994 | Kawasaki et al. |
| 5,531,910 | A | 7/1996 | Severns et al. |
| 5,545,601 | A | 8/1996 | Le-Khac |
| 5,616,679 | A | 4/1997 | Fies et al. |
| 6,359,101 | B1 | 3/2002 | O'Connor et al. |
| 7,355,066 | B1 | 4/2008 | Johnson et al. |
| 10,059,801 | B2 | 8/2018 | Foley et al. |
| 10,844,169 | B2 | 11/2020 | Foley et al. |
| 2004/0152830 | A1 | 8/2004 | Kim et al. |
| 2006/0018977 | A1 | 1/2006 | Bruza et al. |
| 2009/0309220 | A1 | 12/2009 | Katogi et al. |
| 2017/0057940 | A1 | 3/2017 | Foley et al. |
| 2017/0088536 | A1 | 3/2017 | Foley et al. |
| 2017/0283553 | A1 | 10/2017 | Foley et al. |

FOREIGN PATENT DOCUMENTS

| | | |
|---|---|---|
| GB | 1266091 | 3/1972 |
| JP | H09-124780 A | 5/1997 |
| JP | 2002-053648 A | 2/2002 |
| JP | 2002-053649 A | 2/2002 |
| JP | 2003-160649 A | 6/2003 |
| JP | 2003-171460 A | 6/2003 |
| JP | 2006-273796 A | 10/2006 |
| JP | 2008-050415 A | 3/2008 |
| WO | WO 1997/003170 | 1/1997 |
| WO | WO 2001/004178 | 1/2001 |
| WO | WO 2006/057086 | 6/2006 |
| WO | WO 2012/123267 | 9/2012 |

OTHER PUBLICATIONS

Abstract of Japanese Patent Application No. 2006-273796, published Oct. 12, 2006 (1 page).

Abstract of Japanese Patent Application No. 2008-050415, published Mar. 6, 2008 (1 page).

Abstract of DE 10 2005 025 739 A1, published Dec. 7, 2006 (1 page).

Abstract of WO 2006/057086, published Aug. 1, 2006 (1 page).

Bai, et al., "Strategies and Methods for the Synthesis of Anticancer Natural Product Neopeltolide and its Analogs," *Curr Org Chem.*, vol. 19, No. 10, 33 pages, (2015); DOI: 10.2174/1385272819666150119225149.

Cahn, et al., "Specification of Configuration about Quadricovalent Asymmetric Atoms," *J Chem Soc.*, pp. 612-622, (1951); Downloaded by Reprints Desk on Mar. 22, 2016.

Cahn, et al., "The Specification of Asymmetric Configuration in Organic Chemistry," *Experientia*, vol. 12, No. 3, pp. 81-94, (1956).

Cahn, "An Introduction to the Sequence Rule: A System for the Specification of Absolute Configuration," *Journal of Chemical Education*, vol. 41, No. 3, pp. 116-125, (1964).

Cahn, et al., "Specification of Molecular Chirality," *Agnew. Chem. Inter. Edit.*, vol. 5, No. 4, pp. 385-415, (1966).

DaSilva, et al., "Novel Palladium-Catalyzed Oxidative Intramolecular Cyclization of β-Citronellol with $H_2O_2$: A Green and Selective Process to Synthesize Oxocine," *Catalysis Letters*, vol. 147, No. 7, 7 pages (2017), Abstract Only.

Désaubry, et al., "Toward Higher Polyprenols Under 'Prebiotic' Conditions," *Tetrahedron Letters*, Issue 44, pp. 6959-6961, (2003); DOI: 10.1016/S0040-4039(03)01624-1.

Hanson, "Chiral Acylic Synthetic Intermediates from Readily Available Monoterpenoids," *Journal of Chemical Research*, vol. 39, pp. 617-621, (2015).

International Search Report for International Application No. PCT/US2018/044657, mailed Sep. 25, 2018, 4 pages.

Ireland, et al., "The Claisen Rearrangement of N-Allylketene O,N-Acetals," *J.Org.Chem.*, vol. 39, No. 3, pp. 421-424, (1974).

Nagai, "The Formation of Ethers from dl-Citronellol in the Presence of Boron Trifluoride Etherate," *Bulletin of the Chemical Society of Japan*, vol. 49, No. 1, pp. 265-269, (1976).

Nagai, et al., "The Formation of Ethers from Unsaturated Aliphatic Alcohols in the Presence of Boron Trifluoride Etherate," *Bulletin of the Chemical Society of Japan*, vol. 51, No. 11, pp. 3273-3276, (1978).

PubChem CID 13469549, 11 pages, (2007); retrieved on Sep. 10, 2018 from http://pubchem.ncbi.nlm.nih.gov/compound/013469549#section=Top>.

Rashid, et al., "Enzymatic Synthesis of Citronellyl Palmitate in Organic Media: Process Optimization and Kinetic Evaluation," *Asian Journal of Chemistry*, vol. 28, No. 2, pp. 298-300, (2016); http://dx.doi.org/10.14233/ajchem.2016.19276.

Takahashi, et al., "Cationic Polymerization Behavior of Alkoxyallenes," *Macromolecules*, vol. 28, No. 4, pp. 866-869, (1995).

Worzakowska, "Synthesis, Characterization, and Thermal Properties of New Flavor Compounds," *J Therm Anal Calorim*, vol. 116, pp. 727-736, (2014); DOI: 10.1007/s10973-013-3541-1.

Worzakowska, "Thermal Properties of Neryl Long-Chain Esters Obtained Under Microwave Irradiation," *J Therm Anal Calorim*, vol. 120, pp. 1715-1722, (2015); DOI: 10.1007/s10973.015-4489-0.

Written Opinion for International Application No. PCT/US2018/044657, mailed Sep. 25, 2018, 7 pages.

Written Opinion for International Application No. PCT/US2019/21187, mailed Apr. 30, 2019, 7 pages.

Yamashita et al., "Cationic Copolymerization of β, β-Dimethyl-β-propiolactone with 1,30Dioxolane, 3,3-Bis(chloromethyl)oxacyclobutane and Styrene. High-Resolution NMR Studies on Sequence Distribution of Copolymers", *Polymer Journal*, vol. 1, No. 3, p. 327-333, (1970).

POLYETHER DERIVATIVES, USES, AND METHODS OF MAKING THE SAME

CROSS-REFERENCE TO RELATED APPLICATIONS

This application is a U.S. National Stage Application filed under 35 U.S.C. § 371 of International Application No. PCT/US2019/021187, filed Mar. 7, 2019, which claims priority to and the benefit of U.S. Provisional Application Ser. No. 62/639,784, filed on Mar. 7, 2018; the contents of each of which are hereby incorporated by reference in their entireties.

FIELD

The present disclosure is directed to certain polyethers copolymers, and polyether derivatives thereof, and methods of making and using the same. For example, the starting materials may include such species as citronellol, geraniol, linalool, citronellic acid, limonene, dihydromyrcene, myrcenol, adipic acid, propanediol, ethylene glycol, glycerol, 1,9-nonanediol, and 1,6-hexanediol.

BACKGROUND

Liquid polymers have important utility in cosmetic and personal care applications and play critical roles in visual displays, rheology, tribology, and drug delivery. For example, they can be used as lubricants, emollients, or as protective barriers for skin healing and UV protection. Ideally, these materials can be produced in a facile manner, be easily derivatized to modify function, and even more preferably be made from safe and sustainable raw materials.

Monoterpenoid alcohols, such as citronellol, prenol, and isoprenol, are naturally occurring molecules that are also commercially available on a large scale. However, these molecules possess an under-utilized combination of functionalities that allow them to be polymerized and functionalized: an isobutylenic group and an alcohol. Primary alcohols readily undergo nucleophilic addition into highly substituted alkenes to yield ethers. In addition, primary alcohols also readily undergo nucleophilic addition reactions with carboxylic acids and carboxylic acid derivatives to yield esters. As a result, a variety of co-polymerization possibilities exist between monoterpenoid alcohols, diols and dicarboxylic acid derivatives.

This type of chemistry has been mostly neglected in polymer chemistry. One reason for this could be due to the fact that the etherification polymerization is an equilibrium reaction, and that readily abundant isobutylenic alcohols have not always been available. In recent years, however, the production of citronellol, geraniol, linalool, myrcenol, limonene, and nerol have been increasing rapidly, and one of the largest production routes also uses prenol and isoprenol as intermediates, thereby greatly increasing availability.

However, as mentioned above, the equilibrium nature of the polymerization reaction can potentially make it challenging to produce desired ethers on a large scale. There is a need for strategies and methods of production which allow efficient manufacture of these compounds.

BRIEF SUMMARY

In a surprising advancement in polymer science, PCT/US2015/047397 (U.S. equivalent US2017/0283553) and PCT/US2015/016371 (U.S. equivalent US2017/0057940), the contents of each of which are incorporated herein by reference, have taught how to use these functionalities to make new polyether compositions of matter. These polyethers represent an advance in liquid polymer technology and carry with them many desirable benefits for commercial fields of application. In addition, U.S. Provisional Applications 62/539,129 and 62/617,924 (now PCT/US2018/44657, published as WO 2019/028053), the contents of each of which are incorporated herein by reference, have taught how to further derivatize such polyether polymers to increase their functionality and usefulness. The aforementioned patent applications do not, however, disclose polyether polymers comprised of more than one kind of repeating monomeric unit (i.e., these applications disclose homopolymers and derivatives thereof).

The present disclosure builds on the Applicants' own aforementioned patent applications by disclosing novel copolymer compounds derived from one or more of hydroxy alkenes, dienes, diols and dicarboxylic acids (or dicarboxylic acid derivatives), as well as derivatization strategies therefor and methods of production thereof. In still a further aspect, this disclosure teaches methods for controlled release of the monomers contained within these polyether polymers for use in, e.g., fragrance and pest control.

Generally, the present disclosure provides copolymers formed from a combination of monomeric units (i.e., a heteropolymer), wherein the monomeric units comprise at least one $C_{3-14}$alkoxy unit substituted with at least one gem-dimethyl group, and at least one other monomeric unit selected from the group consisting of $C_{1-14}$alkoxy, $C_{5-16}$alkyl, and carbonyl-$C_{2-13}$carbonyloxy.

In some embodiments of the present disclosure, the copolymers comprise at least one unit X and at least one unit Y, wherein the unit X has the formula:

X and wherein the unit Y has a formula selected from Y1, Y2, Y3 and Y4:

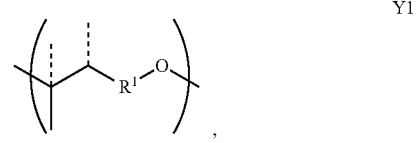

Y1

Y2

Y3

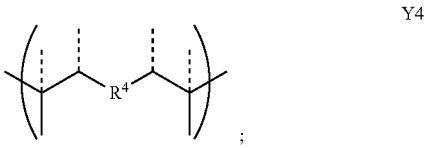

Y4 wherein R, R1, R2, R3 and R4 are as defined hereinafter.

In some embodiments, the copolymer is terminated with at least one terminal unit Z selected from Z, Z1, Z2, Z3, Z4 and Z5:

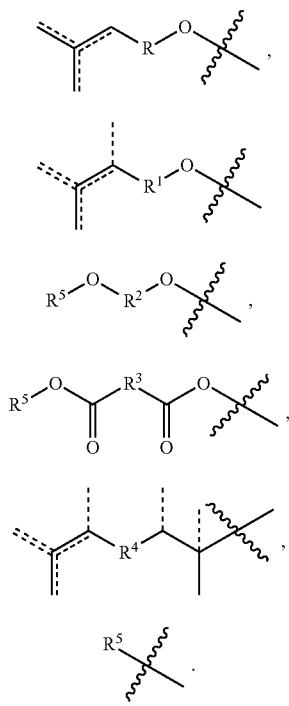

Copolymers according to the present disclosure are prepared from one or more starting materials having the formulas A, A1, A2, A3 and/or A4:

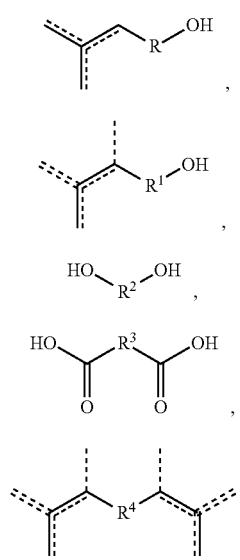

For example, in some embodiments, the copolymer of the present disclosure is a copolymer having the general structure according to Formula Y:

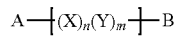

wherein X and Y are as defined above, and wherein A and B are each independently a terminal group selected from Z, Z1, Z2, Z3, Z4 and Z5, and wherein n and m are each independently an integer from 1 to 20. Formula Y thus indicates a linear polymer having from 1 to 20 groups X and from 1 to 20 groups Y, wherein said groups X and groups Y are connected in any linear sequence, wherein the linear polymers is terminated at one end with group A and at the other end with group B.

In further aspects, the present disclosure provides methods of manufacturing said compounds and methods of using said compounds.

DETAILED DESCRIPTION

Figure 1:
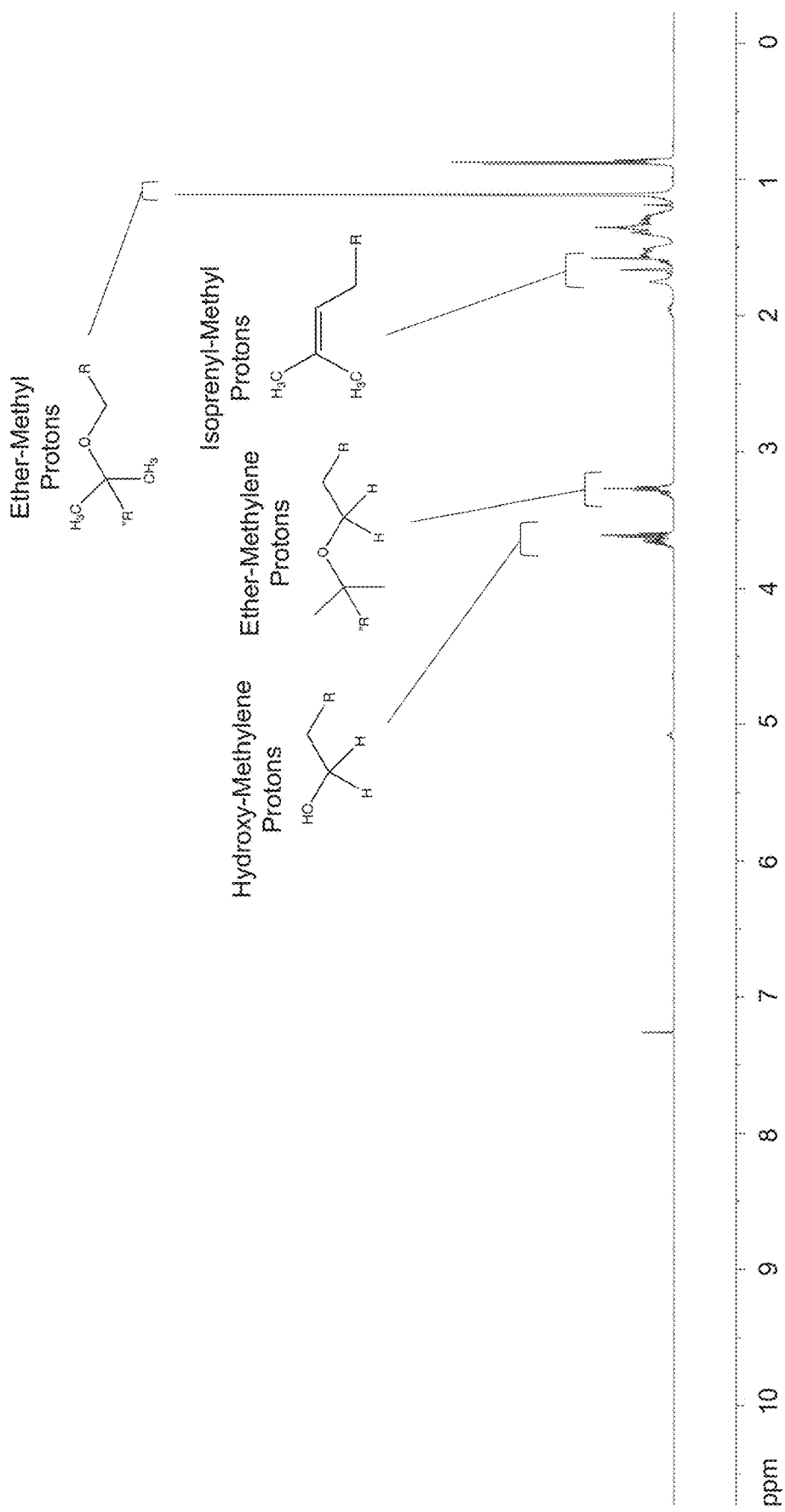
FIG. 1 shows the proton-NMR spectrum obtained according to Example 1 following purification of the product from copolymerization of citronellol and 1,6-hexanediol.

Without wishing to be bound by theory, isobutylenic groups can form ethers with alcohols through an acid catalyzed, mechanism. This chemistry has been used in other instances to make ether bonds in organic synthesis.

The equilibrium nature of this reaction can potentially make it challenging to produce these ethers on a large scale. However, the inventors have discovered that with monomer recycling, proper catalyst selection, and highly concentrated reaction conditions, these molecules can reach sufficient degrees of polymerization in order to be used in a number of different applications. Further, these low molecular weight polymers can be further derivatized to reach much higher molecular weights and to achieve new functionality.

For the purposes of this invention, the term 'citronellol' is meant to include both isomers at the olefinic position. Similarly, when the term 'prenol' is used, it is meant to include isoprenol isomers as well.

While certain methods to make these ethers were described in PCT/US2015/047397 (US2017/0283553), the Applicants have now discovered that these polyethers can be made with even higher degrees of polymerization in a shorter period of time by using a resin-bound acid catalyst, such as Amberlyst®, under neat, solvent-free conditions. In one aspect, these polymerizations can be done at or below room temperature, preferably at slightly elevated temperature, between 30 and 110° C., or even more preferably between 40 and 90° C. (e.g., about 50° C.). Further, in still another aspect, these polymerizations can take place in batch reactors, semi-batch reactors, or even more preferably in continuous packed bed-type reactors of the type described in U.S. Provisional Application 62/384,939 (published as related US 2018/0064108) and PCT/US2017/50808 (published as WO 2018/049252), the contents of each of which are incorporated herein by reference.

Without being bound by theory, the formation of the polyethers can occur in equilibrium under acidic conditions. Therefore, it is unfavorable for these materials to be exposed to acidic conditions during subsequent derivatization, lest depolymerization could take place.

The Applicants have now discovered, however, that transesterification under basic conditions can be accomplished to generate a wide range of new and useful compositions of matter. Further, alkaline Williamson-type etherification can also be accomplished with organohalides. The functionalities that can be produced from these approaches could modify the hydrophilicity, hydrophobicity, and/or viscosity of these polyethers. Further, new functions such as UV protection, antioxidant, anti-aging, skin lightening, antimicrobial, and/or other bioactive activities can be introduced as well.

The unique benefits of the compounds disclosed herein derive from one or more of the following features: the compounds are short-chain polymers; the compounds are made using a reversible polymerization reaction; the polymers are biodegradable and biocompatible; and the polymers may be manufactured using all-natural ingredients. These are important benefits in many of the commercial applications in which these compounds may be used. The compounds disclosed herein are suitable as replacement or substitutes for emollients or surfactants (e.g., octyldodecanol), polymers, and silicones in a variety of commercial products, such as in cosmetics and pharmaceutical compositions, and as adjuvants in crop care formulations, and as lubricants or solvents in enhanced oil recovery, fracking and oil field applications. The compounds disclosed herein offer improved physical characteristics, such as appearance, odor, viscosity, refractive index and/or surface tension. The nature of these compounds as short polymers of moderate molecular weight (e.g., less than 20,000 Daltons, or less than 15,000 Daltons, or less than 10,000 Daltons, or 100-10,000 Daltons, or 100-5,000 Daltons, or 100-3,000 Daltons, or 100-1,500 Daltons).

The reversibility of the polymerization of the disclosed compounds derives from the nature of the polymer, having adjacent oxygen atoms and tertiary carbon atoms. As a result, under conditions which will promote the cleavage of the O—C bond, the resulting tertiary carbocation is unusually stable. This leads to facile abstraction of an adjacent hydrogen atom to regenerate the starting materials' alcohol and alkene functional groups. Such depolymerization may be promoted by mildly acidic conditions (e.g., with Lewis acids or Bronsted acids) or by thermal conditions or by enzymatic conditions (as by enzymes found in naturally occurring bacteria).

This depolymerization property results in biodegradation. This property also permits the formation of compositions comprising the compounds wherein the depolymerization of the polymers may be controlled to permit slow release of the monomeric polymer constituents (e.g. citronellol) or of shortened polymeric constituents (e.g., the release of dimers of citronellol by depolymerization of a larger polymer). The present disclosure embraces solid and/or liquid compositions comprising Copolymer 1, et seq., wherein the formulation provides for slow, controlled depolymerization of the polymers and diffusion of the resulting monomers and or shortened oligomers so that that can be released from the composition (e.g., by vaporization at the surface of the composition). Such formulations may be comprised of ingredients which accelerate such depolymerization (such as Lewis acids or Bronsted acids, or enzymes) or such compositions may be associated with a device comprising an electrical heating element to promote thermal depolymerization. The monomers and/or shortened oligomers produce in this manner (e.g., citronellol or dimers or trimers of citronellol) are themselves beneficial for any number of reasons, e.g., as fragrances, insect repellants, anti-oxidants, anti-microbials, or as active pharmaceutical ingredients (e.g., where the composition is a pharmaceutical composition).

The compounds disclosed herein are particularly suitable for the replacement of silicones, mineral oil and/or paraffins, in cosmetic compositions, such as concealers, primers and/or moisturizers.

In a first aspect, the present disclosure provides a copolymer formed from a combination of monomeric units (i.e., a heteropolymer), wherein the monomeric units comprise at least one $C_{3-14}$ alkoxy unit substituted with at least one gem-dimethyl group, and at least one other monomeric unit selected from the group consisting of $C_{1-14}$alkoxy, $C_{5-16}$alkyl, polyethoxy, and carbonyl-$C_{2-13}$carbonyloxy.

In an embodiment of the first aspect, the present disclosure further provides a copolymer (Copolymer 1) wherein the copolymer comprises at least one unit X and at least one unit Y, wherein the unit X has the formula:

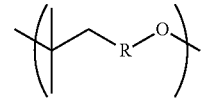

X and wherein the unit Y has a formula selected from Y1, Y2, Y3 and Y4:

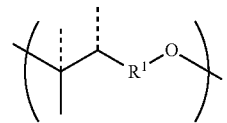

Y1

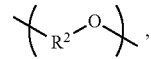

Y2

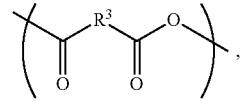

Y3

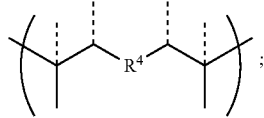

Y4 wherein R, $R^2$, $R^3$, and $R^4$, are each independently optionally substituted $C_1$-$C_{12}$ alkyl, $C_2$-$C_{12}$ alkenyl, or polyethoxy (e.g., $C_1$-$C_{12}$ alkyl or $C_2$-$C_{12}$ alkenyl or polyethoxy, each optionally further substituted with $C_1$-$C_{12}$ alkyl or aryl or hydroxy);
or a salt thereof; and
provided that when the copolymer comprises only groups X and groups Y1 then the substituent R of group X is not the same as the substituent R1 of group Y1.

In further embodiments of the first aspect, the disclosure provides any of the following:

1.1 Copolymer 1, wherein the at least one unit Y is Y1.
1.2 Copolymer 1, wherein the at least one unit Y is Y2
1.3 Copolymer 1, wherein the at least one unit Y is Y3.
1.4 Copolymer 1, wherein the at least one unit Y is Y4.
1.5 Copolymer 1, or any of 1.1-1.4, wherein any one or more of R, $R^2$, $R^3$, and $R^4$, is optionally substituted linear $C_1$-$C_{12}$ alkyl or optionally substituted branched $C_1$-$C_{12}$ alkyl.
1.6 Copolymer 1, or any of 1.1-1.4, wherein any one or more of R, $R^2$, $R^3$, and $R^4$, is unsubstituted linear $C_1$-$C_{12}$ alkyl (e.g., $CH_2$, $CH_2CH_2$ or $CH_2(CH_2)_7CH_2$) or unsubstituted branched $C_3$-$C_{12}$ alkyl (e.g., $CH_2CH_2CH(CH_3)CH_2CH_2$).
1.7 Copolymer 1, or any of 1.1-1.4, wherein any one or more of R, $R^2$, $R^3$, and $R^4$, is unsubstituted linear $C_1$-$C_{12}$ alkyl (e.g., $CH_2$, $CH_2CH_2$ or $CH_2(CH_2)_7CH_2$).
1.8 Copolymer 1, or any of 1.1-1.4, wherein any one or more of R, $R^2$, $R^3$, and $R^4$, is unsubstituted branched $C_3$-$C_{12}$ alkyl (e.g., $CH_2CH_2CH(CH_3)CH_2CH_2$).
1.9 Copolymer 1, or any of 1.1-1.4, wherein any one or more of R, $R^2$, $R^3$, and $R^4$, is $CH_2$.
1.10 Copolymer 1, or any of 1.1-1.4, wherein any one or more of R, $R^1$, $R^2$, $R^3$, and $R^4$, is unsubstituted branched or linear $C_6$ alkyl.
1.11 Copolymer 1, or any of 1.1-1.4, wherein any one or more of R, $R^1$, $R^2$, $R^3$, and $R^4$, is 3-methylpentyl (i.e., $CH_2CH_2CH(CH_3)CH_2CH_2$).
1.12 Copolymer 1, or any of 1.1-1.4, wherein any one or more of R, $R^1$, $R^2$, $R^3$, and $R^4$, is linear hexyl (i.e., $CH_2CH_2CH_2CH_2CH_2CH_2$) or linear nonanyl (i.e., $CH_2CH_2CH_2CH_2CH_2CH_2CH_2CH_2CH_2$).
1.13 Copolymer 1, or any of 1.1-1.4, wherein any one or more of R, $R^1$, $R^2$, $R^3$, and $R^4$, is linear butyl (i.e., $CH_2CH_2CH_2CH_2$) and/or linear propyl (i.e., $CH_2CH_2CH_2$).
1.14 Copolymer 1, or any of 1.1-1.4, wherein any one or more of R, $R^1$, $R^2$, $R^3$, and $R^4$, is ethyl (i.e., $CH_2CH_2$).
1.15 Copolymer 1, or any of 1.1-1.4, wherein any one or more of R, $R^1$, $R^2$, $R^3$, and $R^4$, is $C_{2-12}$ alkenyl (e.g., $C_{2-12}$ alkenyl having from 1 to 4 double bonds).
1.16 Copolymer 1.15, wherein any one or more of R, $R^1$, $R^2$, $R^3$, and $R^4$, is $C_{2-6}$ alkenyl (e.g., $C_{2-6}$ alkenyl having from 1 to 2 double bonds), wherein the alkenyl is linear or branched.
1.17 Copolymer 1.15 or 1.16, wherein any one or more of R, $R^1$, $R^2$, $R^3$, and $R^4$, is $C_6$ alkenyl having one double bond, e.g., a linear hexylene or a methyl-substituted pentylene.
1.18 Copolymer 1.17, wherein any one or more of R, $R^1$, $R^2$, $R^3$, and $R^4$, is 3-methyl-2-pentylene (i.e., $CH_2CH_2C(CH_3)=CHCH_2$) or 3-methyl-3-vinylpropyl (i.e., $CH_2CH_2C(CH_3)CH=CH_2$).
1.19 Copolymer 1, or any of 1.1-1.4, wherein any one or more of R, $R^1$, $R^2$, $R^3$, and $R^4$, is linear nonanyl (i.e., $CH_2CH_2CH_2CH_2CH_2CH_2CH_2CH_2CH_2$).
1.20 Copolymer 1, or any of 1.1-1.4, wherein any one or more of R, $R^1$, $R^2$, $R^3$, and $R^4$, is a hydroxy-substituted $C_{1-12}$ alkyl (e.g., 2-hydroxypropyl, i.e., $CH_2CH(OH)CH_2$).
1.21 Copolymer 1, or any of 1.1-1.4, wherein any one or more of R, $R^1$, $R^2$, $R^3$, and $R^4$, is unsubstituted linear $C_1$-$C_{12}$ alkyl or unsubstituted branched $C_3$-$C_{12}$ alkyl comprising at least one oxygen atom in place of a saturated carbon atom.
1.22 Copolymer 1.21, wherein any one or more of R, $R^1$, $R^2$, $R^3$, and $R^4$, is polyethoxy, e.g., $(OCH_2CH_2)_n$ wherein n is from 1 to 5, e.g., n is 2, 3 or 4.
1.23 Copolymer 1, or any of 1.1-1.22, wherein the copolymer comprises one or more Y units selected from:
a. Y1 wherein $R^1$ is 3-methylpentyl (i.e., $CH_2CH_2CH(CH_3)CH_2CH_2$), e.g., wherein Y1 is

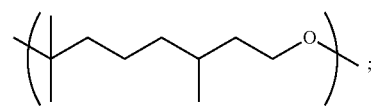

b. Y1 wherein $R^1$ is linear hexyl, e.g., wherein Y1 is

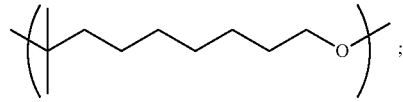

c. Y1 wherein $R^1$ is 3-methyl-2-pentylene (i.e., $CH_2CH_2C(CH_3)=CHCH_2$), e.g., wherein Y1 is

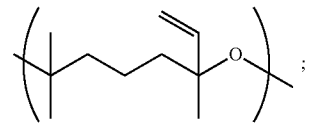

d. Y1 wherein $R^1$ is 3-methyl-3-vinylpropyl (i.e., $CH_2CH_2C(CH_3)CH=CH_2$), e.g., wherein Y1 is

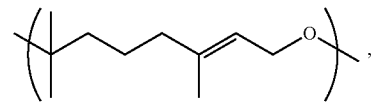

or wherein Y1 is

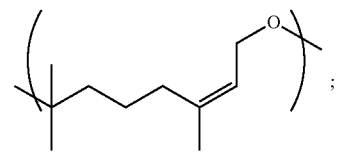

e. Y2 wherein $R^2$ is ethyl;
f. Y2 wherein $R^2$ is linear propyl;
g. Y2 wherein $R^2$ is isopropyl (i.e., $CH_3CHCH_2$);
h. Y2 wherein $R^2$ is linear hexyl;
i. Y2 wherein $R^2$ is linear nonanyl;
j. Y2 wherein $R^2$ is a polyethoxy of the formula $(OCH_2CH_2)$, wherein n is 3;

k. Y2 wherein $R^2$ is 2-hydroxypropyl;
l. Y3 wherein $R^3$ is ethyl;
m. Y3 wherein $R^3$ is linear propyl;
n. Y3 wherein $R^3$ is linear hexyl;
o. Y3 wherein $R^3$ is linear heptyl;
p. Y4 wherein $R^4$ is ethyl (i.e., $CH_2CH_2$), e.g., wherein Y4 is

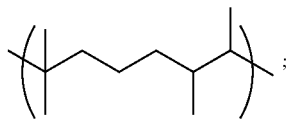

q. Y4 wherein $R^4$ is ethyl (i.e., $CH_2CH_2$), e.g., wherein Y4 is

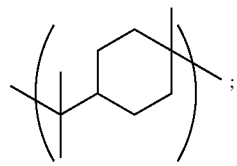

or combinations thereof.

1.24 Copolymer 1 or any of 1.1-1.23, wherein the copolymer comprises one or more units X which are

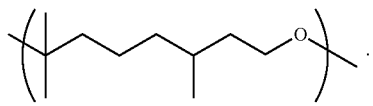

1.25 Copolymer 1, or any of 1.1-1.24, wherein the copolymer consists of one or more units X which are

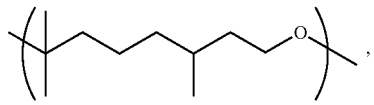

in combination with one or more units Y selected from:
a. Y2 wherein $R^2$ is ethyl;
b. Y2 wherein $R^2$ is linear propyl;
c. Y2 wherein $R^2$ is linear nonanyl; and
d. Y2 wherein $R^2$ is linear hexyl;
or combinations thereof.

1.26 Copolymer 1, or any of 1.1-1.25, wherein the copolymer is a linear polymer comprising from 1 to 20 units X and from 1 to 20 units Y in any order.

1.27 Copolymer 1.26, wherein all of the 1 to 20 units X are the same (i.e. the groups R of the 1-20 units X are the same).

1.28 Copolymer 1.27, wherein the groups R are each unsubstituted branched or linear $C_6$ alkyl.

1.29 Copolymer 1.28, wherein the groups R are each $CH_2CH_2CH(CH_3)CH_2CH_2$.

1.30 Copolymer 1.29, wherein unit X is

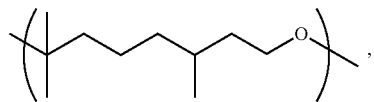

1.31 Any of Copolymers 1.26-1.30, wherein all of the 1 to 20 units Y are the same (e.g., all of the 1 to 20 Y groups are of the formula Y1 with the same $R^1$ group, or all of the 1 to 20 Y groups are of the formula Y2 with the same $R^2$ group, or all of the 1 to 20 Y groups are of the formula Y3 with the same $R^3$ group, or all of the 1 to 20 Y groups are of the formula Y4 with the same $R^4$ group).

1.32 Copolymer 1.31, wherein the X units and Y units are organized in block formation, e.g., wherein the polymer comprises a sequence of monomeric units $(X)n(Y)m$, wherein n and m are each an integer from 1 to 20.

1.33 Any of Copolymers 1.26 to 1.30, wherein all of the 1-20 units Y are of two different formulas, e.g., wherein all of the units Y are combination of units Y2 and units Y3, optionally wherein all of the Y2 units have the same $R^2$ substituent and all of the Y3 units have the same $R^3$ substituent.

1.34 Copolymer 1.33, where in the X and Y units are organized in block formation.

1.35 Copolymer 1.34, wherein the polymer comprises a sequence of monomeric units $(X)n(Y3-Y2)m$, wherein n and m are each from 1 to 25, such that the block of Y units consists of alternating units Y3 and Y2.

1.36 Copolymer 1.35 wherein $R^2$ and $R^3$ are both linear hexyl.

1.37 Copolymer 1 or any of 1.1-1.36, wherein the copolymer is terminated with at least one terminal unit Z selected from Z, Z1, Z2, Z3, Z4 and Z5:

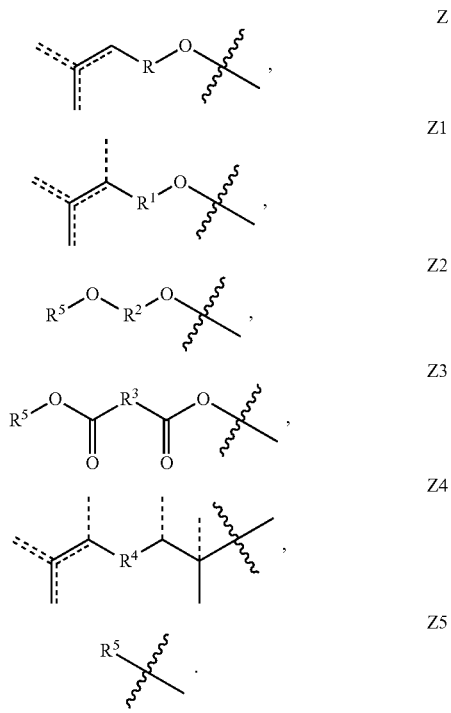

1.38 Copolymer 1.37, wherein the substituent groups R, $R^1$, $R^2$, $R^3$ and/or $R^4$ of the terminal units Z, Z1, Z2, Z3, and/or Z4, as applicable, is/are the same as said groups of the corresponding units X, Y1, Y2, Y3 and/or Y4 of the copolymer.

1.39 Copolymer 1.37, wherein the copolymer is terminated with one or more terminal units Z2, Z3 and/or Z5, wherein $R^5$ is H, OH, $C_{1-20}$ alkyl (e.g., lower alkyl (e.g., $C_{1-6}$ alkyl), or $C_{1-12}$ alkyl), aryl (e.g., phenyl), aryl$C_{1-2}$ alkyl (e.g., benzyl), $OC_{1-20}$ alkyl (e.g., lower alkyl (e.g., $OC_{1-6}$ alkyl), or $OC_{1-12}$ alkyl), O-aryl (e.g., phenoxy), O-aryl$C_{1-2}$ alkyl (e.g., benzyloxy), optionally unsaturated acyl (e.g., C(O)—$C_{1-20}$ alkyl), optionally unsaturated acyloxy (e.g., OC(O)—$C_{1-20}$ alkyl, optionally substituted arylacyl (e.g., C(O)-aryl), or optionally substituted arylacyloxy (e.g., O—C(O)-aryl).

1.40 Copolymer 1.39, wherein $R^5$ is H or OH.

1.41 Copolymer 1.39, wherein $R^5$ is alkyl (e.g., lower alkyl (e.g., $C_{1-6}$), or $C_{1-12}$) or O-alkyl, for example, wherein $R^5$ is:

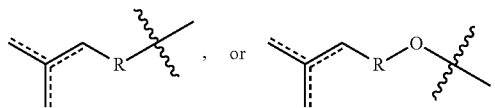

wherein R is defined as provided herein above (i.e., optionally substituted $C_1$-$C_{12}$ alkyl, e.g., $C_1$-$C_{12}$ alkyl optionally further substituted with $C_1$-$C_{12}$ alkyl or aryl, and further embodiments thereof.

1.42 Copolymer 1.39, wherein $R^5$ is selected from methyl, ethyl, propyl, isopropyl, n-butyl, isobutyl, sec-butyl, tert-butyl, n-pentyl, n-hexyl, n-octyl, or n-decyl; or methoxy, ethoxy, propoxy, isopropoxy, n-butyloxy, isobutyloxy, sec-butyloxy, tert-butyloxy, n-pentyloxy, n-hexyloxy, n-octyloxy or n-decyloxy.

1.43 Copolymer 1.39, wherein $R^5$ is aryl$C_{1-2}$ alkyl (e.g., benzyl or phenethyl) or O-aryl$C_{1-2}$ alkyl (e.g., benzyloxy or phenethyloxy).

1.44 Copolymer 1.39, wherein $R^5$ is aryl (e.g., phenyl) or O-aryl (e.g., phenoxy).

1.45 Copolymer 1.39, wherein $R^5$ is an optionally unsaturated acyl (e.g., C(O)—$C_{1-20}$ alkyl, or C(O)—$C_{1-6}$ alkyl) or optionally unsaturated acyloxy (e.g., OC(O)—$C_{1-20}$ alkyl, or OC(O)—$C_{1-6}$ alkyl).

1.46 Copolymer 1.39, wherein $R^5$ is C(O)—$C_{1-6}$ alkyl or OC(O)—$C_{1-6}$ alkyl, optionally wherein $R^5$ is C(O)—$C_{1-5}$ alkyl, C(O)—$C_{1-4}$ alkyl, C(O)—$C_{1-3}$ alkyl, C(O)—$C_{1-2}$ alkyl, OC(O)—$C_{1-5}$ alkyl, OC(O)—$C_{1-4}$ alkyl, OC(O)—$C_{1-3}$ alkyl or OC(O)—$C_{1-2}$ alkyl.

1.47 Copolymer 1.39, wherein $R^5$ is C(O)—$C_{1-6}$ alkyl or OC(O)—$C_{1-6}$ alkyl and said $C_{1-6}$ alkyl is selected from methyl, ethyl, propyl, isopropyl, n-butyl, isobutyl, sec-butyl, tert-butyl, n-pentyl, or n-hexyl.

1.48 Copolymer 1.39, wherein $R^5$ is optionally unsaturated C(O)—$C_{7-20}$ alkyl or OC(O)—$C_{7-20}$ alkyl, optionally wherein $R^5$ is optionally unsaturated C(O)—$C_{10-20}$ alkyl, C(O)—$C_{12-20}$ alkyl, C(O)—$C_{14-20}$ alkyl or C(O)—$C_{16-18}$ alkyl, C(O)—$C_{17}$ alkyl, OC(O)—$C_{10-20}$ alkyl, OC(O)—$C_{12-20}$ alkyl, OC(O)—$C_{14-20}$ alkyl or OC(O)—$C_{16-18}$ alkyl, or OC(O)—$C_{17}$ alkyl.

1.49 Copolymer 1.39, wherein $R^5$ is mono-unsaturated C(O)—$C_{7-20}$ alkyl or OC(O)—$C_{7-20}$ alkyl, optionally wherein $R^5$ is mono-unsaturated C(O)—$C_{10-20}$ alkyl, C(O)—$C_{12-20}$ alkyl, C(O)—$C_{14-20}$ alkyl, C(O)—$C_{16-18}$ alkyl, C(O)—$C_{17}$ alkyl (e.g., oleayl), OC(O)—$C_{10-20}$ alkyl, OC(O)—$C_{12-20}$ alkyl, OC(O)—$C_{14-20}$ alkyl, OC(O)—$C_{16-18}$ alkyl, or OC(O)—$C_{17}$ alkyl (e.g., oleayloxy).

1.50 Copolymer 1.39, wherein $R^5$ is saturated C(O)—$C_{7-20}$ alkyl or OC(O)—$C_{7-20}$ alkyl, optionally wherein $R^5$ is saturated C(O)—$C_{10-20}$ alkyl, C(O)—$C_{12-20}$ alkyl, C(O)—$C_{14-20}$ alkyl, C(O)—$C_{16-18}$ alkyl, C(O)—$C_{17}$ alkyl, OC(O)—$C_{10-20}$ alkyl, OC(O)—$C_{12-20}$ alkyl, OC(O)—$C_{14-20}$ alkyl, OC(O)—$C_{16-18}$ alkyl, or OC(O)—$C_{17}$ alkyl.

1.51 Copolymer 1.39, wherein the $R^5$ substituent is a fatty acyl chain or fatty acyloxy chain.

1.52 Copolymer 1.39, wherein $R^5$ is an arylacyl (e.g., C(O)-aryl) or arylacyloxy (e.g., O—C(O)-aryl), for example, benzoyl or benzyloxy.

1.53 Copolymer 1.39, wherein the $R^5$ substituent further comprises a cationic or anionic moiety (e.g., wherein $R^5$ is alkyl, aryl, alkyl ester, or aryl ester wherein said alkyl or aryl is substituted with a cationic (e.g., quaternary ammonium) or anionic (e.g., carboxylic acid or sulfonic acid) moiety.

1.54 Copolymer 1.39, wherein $R^5$ is a polyether moiety, e.g., wherein the $R^5$ substituent comprises a polyethylene glycol chain.

1.55 Copolymer 1.39, wherein $R^5$ is an anti-aging moiety, UV-absorbing moiety, antioxidant moiety, hydrophobic (lipophilic) moiety, or hydrophilic moiety, as described herein.

1.56 Copolymer 1 or any of 1.1-155, wherein the copolymer has the Formula Y:

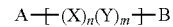

wherein A and B are each independently a terminal group selected from Z, Z1, Z2, Z3, Z4 and Z5, and wherein n and m are each independently an integer from 1 to 20, and wherein the n units X and the m units Y are arranged in a linear sequence in any order.

1.57 A bridged multimer (e.g., dimer) of Copolymer 1 or any of 1.1-1.56, wherein the bridged dimer has the structure W—O—C(O)—$R^6$—C(O)—O—W or W—O—C(O)—O—W, wherein the substituent W is the radical fragment of a Copolymer 1 or any of 1.1-1.56 comprising at least one terminal hydroxy group, e.g., wherein the copolymer has at least (a) a terminal group Z5 wherein $R^5$ is H when the terminal group connects to an O-atom of a monomer unit X, Y1, Y2, Y3 or Y4, or (b) a terminal group Z5 wherein $R^5$ is OH when the terminal group connects to a non-O atom of a monomer unit X, Y1, Y2, Y3, or Y4, or (c) a terminal group Z2 or Z3 wherein $R^5$ is H; and wherein $R^6$ is a bond, or is optionally substituted $C_{1-22}$ alkyl, optionally substituted $C_{2-22}$ alkenyl or optionally substituted aryl; and wherein it is understood that if the fragment W has a second terminal hydroxy group (i.e., a structure HO—W—OH) then the bridged multimer may have a repeating pattern of bridge units and copolymer units, such that the structure is HO—W—O—C(O)—$R^6$—C(O)—[O—WO—C(O)—$R^6$—C(O)]p-O—W—OH or HO—W—O—C(O)—[O—WO—C(O)]p-O—W—OH, wherein p is an integer from 0 to 100 (e.g., from 0-10, or from 0-5 or from 0-3).

1.58 The bridged multimer (e.g., dimer) 1.57, wherein the bridged multimer is formed by reacting a Copolymer 1 or any of 1.1-1.56 comprising one terminal hydroxy group (i.e., W—OH) or two terminal hydroxy groups (i.e., HO—W—OH), with a reactive agent of the formula X—C(O)—R$^6$—C(O)—X, wherein X is a leaving group (e.g., chloro, fluoro, bromo, iodo, alkylsulfonyl, arylsulfonyl, imidazolyl) or wherein X is OH, to form the dimer W—O—C(O)—R$^6$—C(O)—O—W or multimer HO—W—O—C(O)—R$^6$—C(O)—[O—WO—C(O)—R$^6$—C(O)]p-O—W—OH.

1.59 The bridged multimer (e.g., dimer) 1.57, wherein the bridged multimer is formed by reacting a Copolymer 1 or any of 1.1-1.56 comprising one terminal hydroxy group (i.e., W—OH) or two terminal hydroxy groups (i.e., HO—W—OH), with a reactive agent of the formula X—C(O)—X, wherein X is a leaving group (e.g., chloro, fluoro, bromo, iodo, alkylsulfonyl, arylsulfonyl, imidazolyl), to form the dimer W—O—C(O)—O—W or the multimer HO—W—O—C(O)—[O—WO—C(O)]p-O—W—OH.

1.60 The bridged multimer (e.g., dimer) 1.57 or 1.58, wherein the multimer has the structure W—O—C(O)—R$^6$—C(O)—O—W or HO—W—O—C(O)—R$^6$—C(O)—[O—WO—C(O)—R$^6$—C(O)]p-O—W—OH.

1.61 The bridged multimer (e.g., dimer) 1.60, wherein R$^6$ is unsubstituted $C_{1-22}$ alkyl, e.g., linear unsubstituted $C_{1-22}$ alkyl or branched unsubstituted $C_{1-22}$ alkyl.

1.62 The bridged multimer (e.g., dimer) 1.60, wherein R$^6$ is unsubstituted $C_{1-16}$ alkyl, e.g., linear unsubstituted $C_{1-16}$ alkyl or branched unsubstituted $C_{1-16}$ alkyl.

1.63 The bridged multimer (e.g., dimer) 1.60, wherein R$^6$ is unsubstituted $C_{1-10}$ alkyl, e.g., linear unsubstituted $C_{1-10}$ alkyl or branched unsubstituted $C_{1-10}$ alkyl.

1.64 The bridged multimer (e.g., dimer) 1.60, wherein R$^6$ is unsubstituted $C_{1-6}$ alkyl, e.g., linear unsubstituted $C_{1-6}$ alkyl or branched unsubstituted $C_{1-6}$ alkyl.

1.65 The bridged multimer (e.g., dimer) 1.60, wherein R$^6$ is selected from methylene (—CH$_2$—), ethylene (—CH$_2$CH$_2$—), propylene (—CH$_2$CH$_2$CH$_2$— or —CH$_2$CH(CH$_3$)—), butylene (e.g., —CH$_2$CH$_2$CH$_2$CH$_2$— or —CH$_2$CH(CH$_3$)CH$_2$— or —CH(CH$_3$)CH$_2$CH$_2$—).

1.66 The bridged multimer (e.g., dimer) 1.60, wherein R$^6$ is unsubstituted $C_{2-22}$ alkenyl, e.g., linear unsubstituted $C_{2-22}$ alkenyl or branched unsubstituted $C_{2-22}$ alkenyl, optionally wherein any of said alkenyl are mono-unsaturated.

1.67 The bridged multimer (e.g., dimer) 1.60, wherein R$^6$ is unsubstituted $C_{2-16}$ alkenyl, e.g., linear unsubstituted $C_{2-16}$ alkenyl or branched unsubstituted $C_{2-16}$ alkenyl, optionally wherein any of said alkenyl are mono-unsaturated.

1.68 The bridged multimer (e.g., dimer) 1.60, wherein R$^6$ is unsubstituted $C_{2-10}$ alkenyl, e.g., linear unsubstituted $C_{2-10}$ alkenyl or branched unsubstituted $C_{2-10}$ alkenyl, optionally wherein any of said alkenyl are mono-unsaturated.

1.69 The bridged multimer (e.g., dimer) 1.60, wherein R$^6$ is unsubstituted $C_{2-6}$ alkenyl, e.g., linear unsubstituted $C_{2-6}$ alkenyl or branched unsubstituted $C_{2-6}$ alkenyl, optionally wherein any of said alkenyl are mono-unsaturated.

1.70 The bridged multimer (e.g., dimer) 1.60, wherein R$^6$ is selected from ethylene (—CH═CH—), propylene (—CH═CHCH$_2$— or —CH$_2$C(═CH$_2$)—), butylene (e.g., —CH═CHCH$_2$CH$_2$— or —CH$_2$CH═CHCH$_2$— or —CH$_2$CH(═CH$_2$)CH$_2$—).

1.71 The bridged multimer (e.g., dimer) 1.60, wherein R$^6$ is aryl, e.g., substituted or unsubstituted phenyl.

1.72 The bridged multimer (e.g., dimer) 1.60, wherein R$^6$ is a bond.

1.73 The bridged multimer (e.g., dimer) 1.57 or 1.59, wherein the multimer has the structure W—O—C(O)—O—W or HO—W—O—C(O)—[O—WO—C(O)]p-O—W—OH.

It is understood that in the substituent groups bearing optional bonds (e.g., Groups Y1, Y4, Z, Z1 and Z4), all such structures appearing herein embody both the group with each optional bond and the group without each optional bond, and all chemically permissible combinations thereof. For example, the groups Z, Z1 and Z4 encompass at least the following structures, respectively:

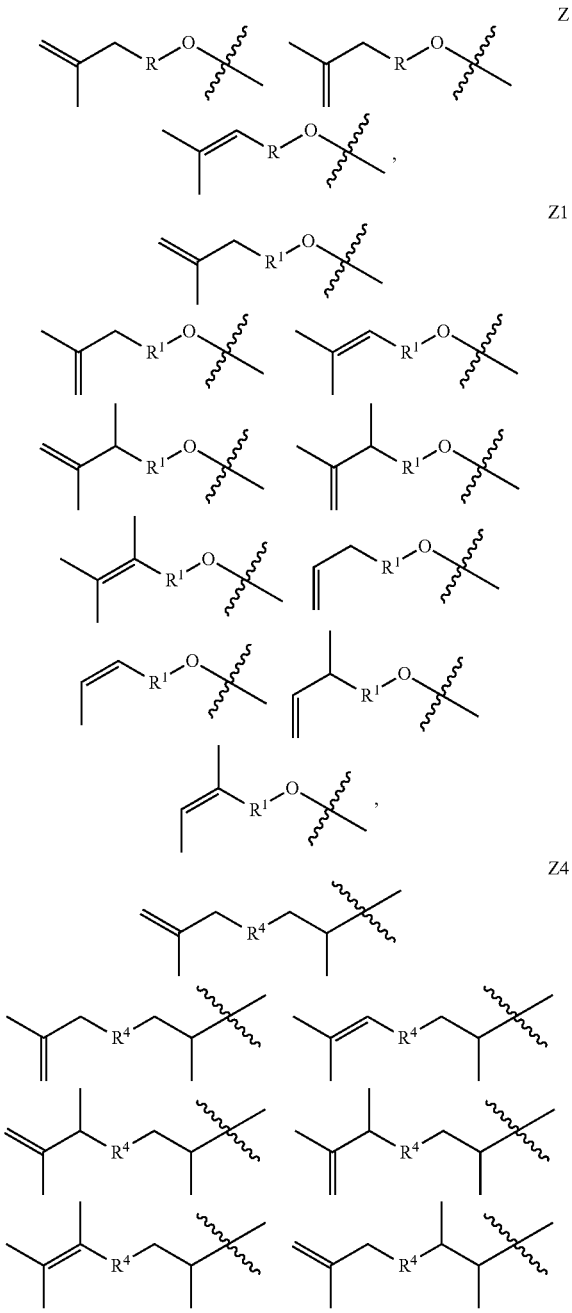

-continued

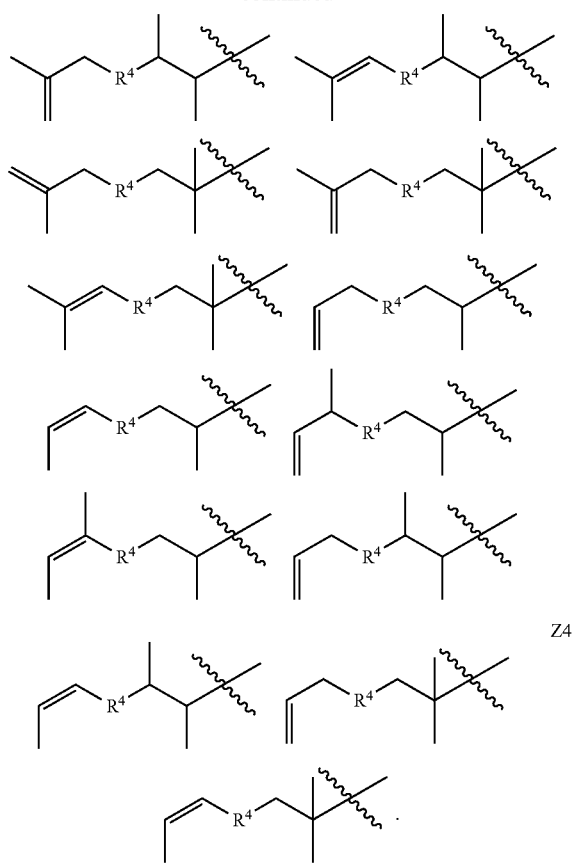

The analogous structures are also encompassed by the monomeric units Y1 and Y4, and the starting material species A, A1 and A4.

In some embodiments, the optional bonds present in monomeric units Y1 and Y4, Z, Z1 and Z4, and starting material species A, A1 and A4, further extend to form intramolecular rings between the optionally bonded atoms. For example, monomeric units Y1 and Y4 encompasses, at least, the following structures:

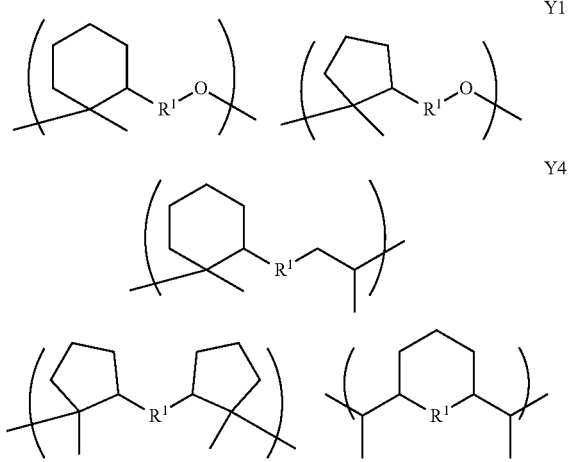

-continued

In second aspect, the present disclosure provides a composition (Composition 1), which composition comprises Copolymer 1 or any of 1.1 et seq., or any salts thereof, or any mixtures thereof, in combination with at least one suitable solvent, carrier, or excipient. In further embodiments of the second aspect, the present disclosure provides Compositions as follows:

1.1 A fragrance composition Copolymer 1 or any of 1.1 et seq., or a salt thereof, or any mixture thereof.

1.2 A perfume composition comprising Copolymer 1 or any of 1.1 et seq., or a salt thereof, or any mixture thereof 1.3 A soap composition comprising Copolymer 1 or any of 1.1 et seq., or a salt thereof, or any mixture thereof 1.4 An insect repellant composition comprising Copolymer 1 or any of 1.1 et seq., or a salt thereof, or any mixture thereof.

1.5 An insecticide composition comprising Copolymer 1 or any of 1.1 et seq., or a salt thereof, or any mixture thereof.

1.6 A detergent composition comprising Copolymer 1 or any of 1.1 et seq., or a salt thereof, or any mixture thereof 1.7 A household cleaning agent composition comprising Copolymer 1 or any of 1.1 et seq., or a salt thereof, or any mixture thereof.

1.8 An air freshener composition comprising Copolymer 1 or any of 1.1 et seq., or a salt thereof, or any mixture thereof.

1.9 A room spray composition comprising Copolymer 1 or any of 1.1 et seq., or a salt thereof, or any mixture thereof.

1.10 A pomander composition comprising Copolymer 1 or any of 1.1 et seq., or a salt thereof, or any mixture thereof 1.11 A candle composition comprising Copolymer 1 or any of 1.1 et seq., or a salt thereof, or any mixture thereof 1.12 Composition 1.11, wherein the composition further comprises a paraffin wax and/or beeswax base.

1.13 Composition 1.12, wherein the composition consists of the Copolymer 1 or any of 1.1 et seq., or a salt thereof, or any mixture thereof, dispersed within the paraffin wax and/or beeswax base, with a suitable wick embedded therein.

1.14 A cosmetic composition comprising Copolymer 1 or any of 1.1 et seq., or a salt thereof, or any mixture thereof, such as, for example, a lipstick, lip balm, lip gloss, eye shadow, liquid highlighter (e.g., for the cheeks), a skin ointment, skin lotion, or a skin balm.

1.15 A toilet water composition comprising Copolymer 1 or any of 1.1 et seq., or a salt thereof, or any mixture thereof.

1.16 A pre- and/or aftershave lotion composition comprising Copolymer 1 or any of 1.1 et seq., or a salt thereof, or any mixture thereof.

1.17 A talcum powder composition comprising Copolymer 1 or any of 1.1 et seq., or a salt thereof, or any mixture thereof.

1.18 A hair-care product composition comprising Copolymer 1 or any of 1.1 et seq., or a salt thereof, or any mixture thereof, for example, a hair styling product (e.g., hair spray, hair gel, or hair drying cream, mousse) or hair cleaning product (e.g., shampoo or conditioner).

1.19 A body deodorant composition comprising Copolymer 1 or any of 1.1 et seq., or a salt thereof, or any mixture thereof.

1.20 An anti-perspirant composition comprising Copolymer 1 or any of 1.1 et seq., or a salt thereof, or any mixture thereof.

1.21 A shampoo composition comprising Copolymer 1 or any of 1.1 et seq., or a salt thereof, or any mixture thereof 1.22 A pet litter composition comprising Copolymer 1 or any of 1.1 et seq., or a salt thereof, or any mixture thereof 1.23 A topically applied skin care composition comprising Copolymer 1 or any of 1.1 et seq., or a salt thereof, or any mixture thereof, optionally wherein the skin care application may be selected from skin-conditioning agents; skin penetration enhancing agents; skin protectants; skin soothing agents; skin healing agents; ultraviolet light absorbers or scattering agents; sequestrants; anti-acne agents; anti-androgens; depilation agents; keratolytic agents/desquamation agents/exfoliants such as salicylic acid; panthenol moisturizer such as D-panthenol; soluble or colloidally-soluble moisturizing agents such as hyaluronic acid and starch-grafted sodium polyacrylates; and sunscreens.

1.24 Composition 1.23, wherein the skin care application is a skin protectant.

1.25 Composition 1.23, wherein the skin care application is a skin soothing agent or skin moisturizing agent (e.g., in a moisturizing lotion).

1.26 Composition 1.23, wherein the skin care application is a sunscreen.

1.27 A paint or coating composition comprising Copolymer 1 or any of 1.1 et seq., or a salt thereof, or any mixture thereof.

1.28 A lubricant composition comprising Copolymer 1 or any of 1.1 et seq., or a salt thereof, or any mixture thereof 1.29 A plastic composition comprising Copolymer 1 or any of 1.1 et seq., or a salt thereof, or any mixture thereof 1.30 A defoamer composition comprising Copolymer 1 or any of 1.1 et seq., or a salt thereof, or any mixture thereof 1.31 A hydraulic fluid composition comprising Copolymer 1 or any of 1.1 et seq., or a salt thereof, or any mixture thereof.

1.32 An antimicrobial composition comprising Copolymer 1 or any of 1.1 et seq., or a salt thereof, or any mixture thereof.

1.33 A crop care formulation comprising Copolymer 1 or any of 1.1 et seq., e.g., wherein said compound is an adjuvant in the crop care formulation.

1.34 A formulation for enhanced oil recovery, fracking and/or other oil field applications comprising Copolymer 1 or any of 1.1 et seq., e.g., wherein said compound is lubricant or solvent in said formulation.

1.35 A composition comprising, or consisting of, Copolymer 1 or any of 1.1 et seq., dissolved or suspended in a solvent or mixture of solvents, e.g., ester, alkane, aromatic, alcohol, or ether solvents.

1.36 A solution or suspension of Copolymer 1 or any of 1.1 et seq., in a solvent or mixture of solvents, e.g., ester, alkane, aromatic, alcohol, or ether solvents.

1.37 Composition 1.35 or 1.36, wherein the solvents are selected from $C_{1-4}$ esters (e.g., methyl acetate, ethyl acetate, isopropyl acetate), $C_{4-18}$ esters, $C_{3-10}$ alkanes (e.g., hexane, heptane, octane), $C_{10-18}$ alkanes (linear or branched), $C_{2-10}$ alcohols (e.g., ethanol, propanol, isopropanol), $C_{2-10}$ ethers (e.g., diethyl ether, diisopropyl ether, methyl tert butyl ether, tetrahydrofuran, dioxane), and $C_{6-12}$ aromatics (e.g., toluene, xylenes).

1.38 A product comprising any preceding composition wherein said composition is stored or housed in a receptacle comprising an electrical heating element, wherein actuation of the heating element results in heating of the composition, thermal decomposition of the Compound, and release of volatile substances.

In another embodiment, the present disclosure provides Copolymer 1, or any of 1.1-1.73, for use in Composition 1, or any of 1.1-1.38.

In a third aspect, the disclosure provides a method of making Copolymer 1 or any of 1.1 et seq., wherein the method comprises the steps of (1) introducing into a reactor a compound of Formula A:

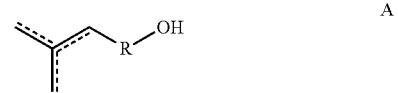

A and at least one of a compound of Formula A1, A2, A3 or A4,

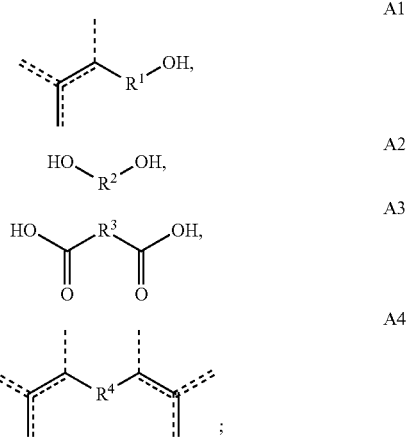

A1

A2

A3

A4 wherein, each of R, $R^1$, $R^2$, $R^3$, $R^4$ and/or is optionally substituted $C_1$-$C_{12}$ alkyl, $C_2$-$C_{12}$ alkenyl, or polyethoxy (e.g., $C_1$-$C_{12}$ alkyl or $C_2$-$C_{12}$ alkenyl or polyethoxy, each optionally further substituted with $C_1$-$C_{12}$ alkyl or aryl or hydroxy);

and (2) exposing said compound to a solid ion-exchange resin, thereby causing the copolymerization of the compound of Formula A with the compound of Formula A1, A2, A3 and/or A4, to yield a copolymer according to Copolymer 1 or any of 1.1-1.56, wherein if $R^5$ is present then $R^5$ is H;

and (3) isolating and/or purifying (e.g., by distillation) the Copolymer 1, e.g., a group of related Copolymers 1 having the same or substantially the same monomeric composition.

In further embodiments of the third aspect, the disclosure provides the following:

1.1 Method 1, wherein the polymerization occurs over the ion-exchange resin at elevated temperature (e.g., between 30 and 120° C.).

1.2 Method 1.1, wherein the polymerization occurs over the ion-exchange resin at between 40 and 90° C.

1.3 Method 1.2, wherein the polymerization occurs over the ion-exchange resin at about 50° C.

1.4 Method 1 or any of 1.1-1.4, wherein the solid exchange resin is a resin-bound acid catalyst, e.g., a resin functionalized with carboxylic acid or sulfonic acid moieties.

1.5 The method of any of the preceding methods, wherein the polymerization of occurs in a batch reactor.

1.6 The method of any of the preceding methods, wherein the polymerization occurs in a continuous packed-bed reactor.

1.7 The method of any of the preceding methods, wherein the monomers of Formula A are polymerized by acid catalysis, followed by distillation and recycling of any unpolymerized monomer.

1.8 The method of any of the preceding methods, wherein the resin-bound acid catalyst is selected from Silicycle propanesulfonic acid, montmorillonite, or Amberlyst® (e.g., macroreticular or cellular resins or silica covalently bonded to sulfonic acid or carboxylic acid groups).

1.9 The method of 1.7, wherein the catalyst is Amberlyst®.

1.10 The method of any of the preceding methods, wherein the Copolymer 1 is purified by fractional distillation.

1.11 The method of any of the preceding methods, further comprising the step of reacting a Copolymer 1 wherein the copolymer includes at least one terminal hydroxy group (e.g., a group $R^5$, wherein $R^5$ is H or OH, depending on the connectivity of group $R^5$ to the copolymer), with a suitable reagent to convert the terminal hydroxy group to an alkyl ester or aryl ester moiety (e.g., to produce any of Copolymers 1.41-1.55, or embodiments thereof), for example, wherein the alkyl ester is a methyl ester and the reaction uses ketene as the suitable reagent.

1.12 Method 1.11, wherein the esterification is an alkaline transesterification using a functionalized ester.

1.13 Method 1, or any of 1.1-1.10, further comprising the step of reacting the Copolymer 1 wherein the copolymer includes at least one terminal hydroxy group (e.g., a group $R^5$, wherein $R^5$ is H or OH, depending on the connectivity of group $R^5$ to the copolymer), with a suitable reagent to convert to the terminal hydroxy group to an alkyl ether or aryl ether moiety (e.g., to produce any of Compounds 1.41-1.55, or embodiments thereof).

1.14 Method 1.13, wherein the etherification is a Williamson-type etherification reaction using a suitable alkyl halide and a base.

1.15 Method 1, or any of 1.1-1.14, further comprising the step of reacting the Copolymer 1 wherein the copolymer includes at least one terminal hydroxy group (e.g., a group $R^5$, wherein $R^5$ is H or OH, depending on the connectivity of group $R^5$ to the copolymer), with a suitable reagent to convert the copolymer to a bridged dimer according to any of Compound 1.57 to 1.73.

1.16 Method 1.15, wherein the bridged dimer has the formula W—O—C(O)—O—W and the suitable reagent is phosgene.

1.17 Method 1.15, wherein the bridged dimer has the formula W—O—C(O)—$R^6$—C(O)—O—W, and the suitable reagent is a diacid of the formula HO—C(O)—$R^6$—C(O)—OH.

1.18 Method 1.15, wherein the bridged dimer has the formula W—O—C(O)—$R^6$—C(O)—O—W, and the suitable reagent is a reactive diacyl species of the formula XO—C(O)—$R^6$—C(O)—OX, wherein X is a leaving group (e.g., chloro, fluoro, bromo, iodo, alkylsulfonyl (e.g., methanesulfonyl or ethanesulfonyl), aryl sulfonyl (e.g., benzenesulfonyl or toluenesulfonyl), imidazolyl).

In another embodiment, the present disclosure provides a copolymer made according to Method 1, or any of Methods 1.1-1.18.

Exemplary monomeric species suitable for use to make any of Copolymer 1 or 1.1 et seq., or suitable for use in Method 1 or any of Methods 1.1-1.18, include, but are not limited to, acyclic monoterpenoid alcohols (such as citronellol, geraniol, nerol, linalool, licareol, coriandrol, myrcenol, and dihydromyrcenol; cyclic monoterpenoid alcohols (such as isopulegol, and menthol), acyclic monoterpenes (such as dihydromyrcene); alkane diols (such as 1,9-nonanediol, 1,6-hexanediol, 1,4-butanediol, 1,3-propylene glycol, 1,2-propylene glycol, glycerol, and ethylene glycol); polyethylene glycols such as diethylene glycol, triethylene glycol, and tetraethylene glycol); and dicarboxylic acids (such as azelaic acid, adipic acid and succinic acid). Additional species which may take part in the formation of Copolymer 1 or 1.1 et seq., or which may be suitable for use in Method 1 or 1.1-1.18, include dienes (such as 1,3-butadiene, 1,4-pentadiene, 1,5-hexadiene, 2,6-octadiene, and limonene), and alkene acids (such as citronellic acid).

In particular embodiments, the Copolymer 1 may be made according to Method 1 or any of 1.1-1.18 using a combination of (1) citronellol monomer, and (2) one or more monomers selected from 1,6-hexanediol, linalool, geraniol, nerol, limonene (e.g., d-limonene), glycerol, dihydromyrcene, triethylene glycol, 1,3-propanediol, 1,2-propanediol, 1,9-nonanediol and ethylene glycol. In further embodiments, the Copolymer 1 may be made according to Method 1 or any of 1.1-1.18 using a combination of (1) citronellol monomer, and (2) one or more monomers selected from 1,6-hexanediol, 1,3-propanediol, 1,2-propanediol, 1,9-nonanediol and ethylene glycol.

In some embodiments, UV absorbing moieties include, but are not limited to, conjugated aromatic esters, conjugated aromatic ethers, and conjugated olefins. Specific examples include, but are not limited to, cinnamic acid, cinnamic acid derivatives, salicylic acid, salicylic acid derivatives, dimethylaminobenzoic acid, para-aminobenzoic acid, benzoic acid, 3,3-diphenylcyanoacrylate, diethylamino hydroxybenzoyl benzoate, and methoxycinnamic acid.

In some embodiments, the anti-aging and/or antioxidant moieties include, but are not limited to, hyaluronic acid, ascorbic acid, azelaic acid, carnosine, glycolic acid, nicotinic acid, phenolic acids, phenol ethers, benzophenones, sulfites, sulfones, sulfonates, and phosphates.

In some embodiments, hydrophobic moieties include acetate, propionate, linear or branched fatty acids, linear or branched alkyl chains, organosilicones, fluoroalkanes, and graphene derivatives. Hydrophilic moieties include sulfonates, ethoxylates, polyglycerol, polypropylene glycol, carbohydrates, and, carboxylic acids, and other polyols.

Copolymer 1 et seq., e.g., for example, as produced according to Method 1, et seq., could also be connected to (e.g., esterified or etherified to) other biologically active molecules, such as antimicrobial compounds, pharmaceutical compounds, skin-healing compounds, and sensient molecules, such as cooling agents, anti-inflammatory agents, and/or warming agents.

Copolymer 1, et seq., e.g., as produced by Method 1, et seq., could be used for many applications. They can be used in cosmetic formulations, in paints or coatings, in personal care products, in household products, e.g., in cleaning products, in electronics, in lubricants, in plastics, in defoamers, in enhanced oil and gas recovery (including fracking and other oil field applications), in pharmaceutical applications, in crop care formulations, and in hydraulic fluids. The compounds disclosed herein are suitable as replacements or substitutes for surfactants, polymers, silicones, and solvents in these various applications. These materials, particularly the lower molecular weight molecules, can also be used beneficially as insect repellents. For example, Copolymer 1, et seq., e.g., as produced by the methods of Method 1 et seq., can be used or incorporated with insecticides, insect-repellent and bioactive ingredients.

In a fourth aspect the, the present disclosure provides a method of using Copolymer 1 et seq., e.g., produced by Method 1, et seq., in a composition (e.g., Composition 1, et seq., for example, a fragrance composition, perfume, soap, insect repellant and insecticide, detergent, household cleaning agent, air freshener, room spray, pomander, candle, cosmetic, toilet water, pre- and aftershave lotion, talcum powder, hair-care product, body deodorant, anti-perspirant, shampoo, skin care applications, pharmaceuticals, antimicrobials, pet litter, crop care formulation, or oil field, fracking or enhanced oil recovery formation).

Thus, the present disclosure provides a method (Method 2) of using Copolymer 1, or any of 1.1-1.73, in the manufacture of Composition 1, or any of Compositions 1.1-1.38.

In further embodiments of the fourth aspect, Method 2 may provide any of the following:

2.1 The method of Method 2, wherein Copolymer 1 or any of 1.1-1.73, is used in a fragrance composition.
2.2 The method of Method 2, wherein Copolymer 1 or any of 1.1-1.73, is used in a perfume.
2.3 The method of Method 2, wherein Copolymer 1 or any of 1.1-1.73, is used in a soap.
2.4 The method of Method 2, wherein Copolymer 1 or any of 1.1-1.73, is used in an insect repellant.
2.5 The method of Method 2, wherein Copolymer 1 or any of 1.1-1.73, is used in an insecticide.
2.6 The method of Method 2, wherein Copolymer 1 or any of 1.1-1.73, is used in a detergent.
2.7 The method of Method 2, wherein Copolymer 1 or any of 1.1-1.73, is used in a household cleaning agent.
2.8 The method of Method 2, wherein Copolymer 1 or any of 1.1-1.73, is used in an air freshener.
2.9 The method of Method 2, wherein Copolymer 1 or any of 1.1-1.73, is used in a room spray.
2.10 The method of Method 2, wherein Copolymer 1 or any of 1.1-1.73, is used in a pomander.
2.11 The method of Method 2, wherein Copolymer 1 or any of 1.1-1.73, is used in a candle.
2.12 The method of Method 2, wherein Copolymer 1 or any of 1.1-1.73, is used in a cosmetic.
2.13 The method of Method 2, wherein Copolymer 1 or any of 1.1-1.73, is used in a toilet water.
2.14 The method of Method 2, wherein Copolymer 1 or any of 1.1-1.73, is used in a pre- and aftershave lotion.
2.15 The method of Method 2, wherein Copolymer 1 or any of 1.1-1.73, is used in a talcum powder.
2.16 The method of Method 2, wherein Copolymer 1 or any of 1.1-1.73, is used in a hair-care product.
2.17 The method of Method 2, wherein Copolymer 1 or any of 1.1-1.73, is used in a body deodorant.
2.18 The method of Method 2, wherein Copolymer 1 or any of 1.1-1.73, is used in an anti-perspirant.
2.19 The method of Method 2, wherein Copolymer 1 or any of 1.1-1.73, is used in a shampoo.
2.20 The method of Method 2, wherein Copolymer 1 or any of 1.1-1.73, is used in a pet litter.
2.21 The method of Method 2, wherein Copolymer 1 or any of 1.1-1.73, is used in a topically applied in a skin care application, wherein the skin care application may be selected from skin-conditioning agents; skin penetration enhancing agents; skin protectants; skin soothing agents; skin healing agents; ultraviolet light absorbers or scattering agents; sequestrants; anti-acne agents; anti-androgens; depilation agents; keratolytic agents/desquamation agents/exfoliants such as salicylic acid; panthenol moisturizer such as D-panthenol; soluble or colloidally-soluble moisturizing agents such as hyaluronic acid and starch-grafted sodium polyacrylates; and sunscreens.
2.22 The method of Method 2.21, wherein the skin care application is a skin protectant.
2.23 The method of Method 2.21, wherein the skin care application is a skin soothing agent.
2.24 The method of Method 2.21, wherein the skin care application is a sunscreen.
2.25 The method of Method 2, wherein Copolymer 1 or any of 1.1-1.73, is used in a paint or coating.
2.26 The method of Method 2, wherein Copolymer 1 or any of 1.1-1.73, is used in a lubricant.
2.27 The method of Method 2, wherein Copolymer 1 or any of 1.1-1.73, is used in a plastic.
2.28 The method of Method 2, wherein Copolymer 1 or any of 1.1-1.73, is used in a pharmaceutical.
2.29 The method of Method 2, wherein Copolymer 1 or any of 1.1-1.73, is used in a crop care formulation, e.g., wherein said compound is an adjuvant in the crop care formulation.
2.30 The method of Method 2, wherein Copolymer 1 or any of 1.1-1.73, is used in a formulation for enhanced oil recovery, fracking and/or other oil field applications, e.g., wherein said compound is lubricant or solvent in said formulation.

An added benefit of these materials described herein is that they are expected to be fully biodegradable and biocompatible.

During the course of the evaluation of these polyethers, it was surprisingly observed that the depolymerization back to monomer would spontaneously occur at −180° C. for the citronellol-based polymers. This thermal depolymerization property, or similar enzymatic and/or, acid catalyzed depolymerization properties could be beneficially used to deliver citronellol monomer in a controlled fashion over time.

In one aspect, thermal depolymerization could be used to deliver monomer into the air in a controlled release. In one aspect, the invention contemplates using the compounds of Copolymer 1, et seq., e.g., as produced by Method 1, et seq., e.g., in candles or thermal dispensers used for odor control and/or mosquito control, in low pH industrial cleaners which could have the depolymerized monomer ingredient released over time to promote beneficial odor, and laundry detergents that could use enzymes to digest the polymers over time to have fresh odor over longer periods.

In another aspect, the fragrance compositions of the present application, comprising the compounds of Copolymer 1, et seq., e.g., as produced by Method 1, et seq., and the fragrance composition is selected from: perfumes, soaps, insect repellants and insecticides, detergents, household cleaning agents, air fresheners, room sprays, pomanders, candles, cosmetics, toilet waters, pre- and aftershave lotions, talcum powders, hair-care products, body deodorants, antiperspirants, shampoo, cologne, shower gel, hair spray and pet litter.

In another aspect, the compounds of Copolymer 1, et seq., e.g., as produced by Method 1, et seq., may be used in an antifungal composition. In aspect the antifungal composition comprises a polyethers of Copolymer 1, et seq., e.g., as produced by Method 1, et seq., and at least one type of compound that demonstrates synergistic effects in the presence of the above fragrance component selected from the group consisting of aliphatic or aromatic aldehydes, aliphatic or aromatic alcohols, acetal and ester, thereby making it possible to reduce the contained amounts of active ingredients to a lower amount than in the case of using each alone.

In another aspect the compounds of Copolymer 1, et seq., e.g., as produced by Method 1, et seq., may be used topically applied in a skin care application. For example, the skin care application may be selected from skin-conditioning agents; skin penetration enhancing agents; skin protectants; skin soothing agents; skin healing agents; ultraviolet light absorbers or scattering agents; sequestrants; anti-acne agents; anti-androgens; depilation agents; keratolytic agents/desquamation agents/exfoliants such as salicylic acid; panthenol moisturizer such as D-panthenol; soluble or colloidally-soluble moisturizing agents such as hyaluronic acid and starch-grafted sodium polyacrylates; and sunscreens.

In another aspect, the polyethers of Copolymer 1, et seq., as produced by Method 1 et seq., may be used in a delivery system, for example, in any fragrance delivery system in which a prolonged, defined release of the above-mentioned fragrant compounds is desired. For example, fragrance delivery systems as described herein may be used, e.g., in functional perfumery, in articles which are exposed to daylight when in use or which are applied to other articles which thereafter are exposed to daylight.

Further embodiments, the present disclosure provides Delivery System 4.0 which includes, e.g., air-fresheners in liquid and solid form which, with the delivery system of the present invention. Still further examples include delivery systems which deliver window and household cleaners, all purpose-cleaners and furniture polish. The surfaces which have been cleaned with such cleaners. In a further example, the delivery system includes detergents and fabric softeners can also contain the delivery system of the present invention, and the clothes washed or treated with such detergents or softeners.

In still another aspect the polyethers of Copolymer 1, et seq., e.g., as produced by Method 1 et seq., may be used in a drug delivery system.

In certain embodiments, the Delivery system 4.0 may comprise any of the following Delivery systems:

4.1 A drug delivery system comprising a Copolymer 1 or any of 1.1-1.73, or any salt thereof, or mixtures thereof.

4.2 A fragrance delivery system comprising a Copolymer 1 or any of 1.1-1.73, or any salt thereof, or mixtures thereof.

4.3 A detergent delivery system comprising a Copolymer 1 or any of 1.1-1.73, or any salt thereof, or mixtures thereof.

4.4 A household cleaner delivery system comprising a Copolymer 1 or any of 1.1-1.73, or any salt thereof, or mixtures thereof.

The details of one or more embodiments of the invention are set forth in the accompanying description below. Unless defined otherwise, all technical and scientific terms used herein have the same meaning as commonly understood by one of ordinary skill in the art to which this invention belongs. In the case of conflict, the present specification will control.

Unless otherwise indicated, it is to be understood that the terminology used herein is for the purpose of describing particular embodiments only and is not intended to be limiting. In this specification and in the claims that follow, reference will be made to a number of terms, which shall be defined to have the definitions set forth below.

As used herein, the singular forms "a," "an," and "the" include plural referents unless the context clearly dictates otherwise. Thus, for example, reference to "a reactant" includes not only a single reactant but also a combination or mixture of two or more different reactant, reference to "a substituent" includes a single substituent as well as two or more substituents, and the like.

As used herein, the phrases "for example," "for instance," "such as," or "including" are meant to introduce examples that further clarify more general subject matter. These examples are provided only as an aid for understanding the disclosure, and are not meant to be limiting in any fashion. Furthermore, as used herein, the terms "may," "optional," "optionally," or "may optionally" mean that the subsequently described circumstance may or may not occur, so that the description includes instances where the circumstance occurs and instances where it does not. For example, the phrase "optionally present" means that an object may or may not be present, and, thus, the description includes instances wherein the object is present and instances wherein the object is not present.

As used herein, the phrase "having the formula" or "having the structure" is not intended to be limiting and is used in the same way that the term "comprising" is commonly used.

In some formulae of the present application, one or more chiral centers are identified by an asterisk placed next to the chiral carbon. In other formulae, no chiral center is identified, but the chiral isomers are nonetheless covered by these formulae.

Some compounds of the present invention can exist in a tautomeric form which is also intended to be encompassed within the scope of the present invention.

"Tautomers" refers to compounds whose structures differ markedly in arrangement of atoms, but which exist in easy and rapid equilibrium. It is to be understood that the compounds of the invention may be depicted as different tautomers. it should also be understood that when compounds have tautomeric forms, ail tautomeric forms are intended to be within the scope of the invention, and the naming of the compounds does not exclude any tautomeric form. Further, even though one tautomer may be described, the present invention includes all tautomers of the present compounds.

As used herein, the term "salt" can include acid addition salts including hydrochlorides, hydrobromides, phosphates, sulfates, hydrogen sulfates, alkyl sulfonates, arylsulfonates, acetates, benzoates, citrates, maleates, fumarates, succinates, lactates, and tartrates; alkali metal cations such as Na+, K+, Li+, alkali earth metal salts such as $Mg^{2+}$ or $Ca^{2+}$, or organic amine salts, or organic phosphonium salts.

The term "alkyl" as used herein refers to a monovalent or bivalent, branched or unbranched saturated hydrocarbon group having from 1 to 22 carbon atoms, typically although, not necessarily, containing 1 to about 12 carbon atoms, such as methyl, ethyl, n-propyl, isopropyl, n-butyl, isobutyl, t-butyl, octyl, and the like. The term alkyl also may include cycloalkyl groups. Thus, for example, the term $C_6$ alkyl would embrace cyclohexyl groups. For example, in some embodiments, R, $R_1$, $R_2$, $R_3$, or $R_4$ may be a $C_{6-12}$ alkyl group comprising a cyclohexane ring, e.g., selected from:

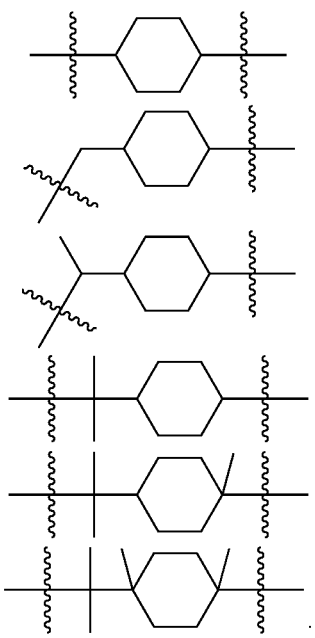

The term "alkenyl" as used herein refers to a monovalent or bivalent, branched or unbranched, unsaturated hydrocarbon group typically although not necessarily containing 2 to about 12 carbon atoms and 1-10 carbon-carbon double bonds, such as ethylene, n-propylene, isopropylene, n-butylene, isobutylene, t-butylene, octylene, and the like.

The term "alkynyl" as used herein refers to a monovalent or bivalent, branched or unbranched, unsaturated hydrocarbon group typically although not necessarily containing 2 to about 12 carbon atoms and 1-8 carbon-carbon triple bonds, such as ethyne, propyne, butyne, pentyne, hexyne, heptyne, octyne, and the like.

The term "aryl" as used herein refers to an aromatic hydrocarbon moiety comprising at least one aromatic ring of 5-6 carbon atoms, including, for example, an aromatic hydrocarbon having two fused rings and 10 carbon atoms (i.e, naphthalene).

By "substituted" as in "substituted alkyl," "substituted alkenyl," "substituted alkynyl," and the like, it is meant that in the alkyl, alkenyl, alkynyl, or other moiety, at least one hydrogen atom bound to a carbon atom is replaced with one or more non-hydrogen substituents, e.g., by a functional group.

The terms "branched" and "linear" (or "unbranched") when used in reference to, for example, an alkyl moiety of $C_a$ to $C_b$ carbon atoms, applies to those carbon atoms defining the alkyl moiety. For example, for a $C_4$ alkyl moiety, a branched embodiment thereof would include an isobutyl, whereas an unbranched embodiment thereof would be an n-butyl. However, an isobutyl would also qualify as a linear $C_3$ alkyl moiety (a propyl) itself substituted by a $C_1$ alkyl (a methyl).

Examples of functional groups include, without limitation: halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO−), carbamoyl (—(CO)—NH$_2$), mono-substituted $C_1$-$C_{24}$ alkylcarbamoyl (—(CO)—NH($C_1$-$C_{24}$ alkyl)), di-substituted alkylcarbamoyl (—(CO)—N($C_1$-$C_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano (—C≡N), isocyano (—N+≡C−), cyanato isocyanato (—O—N+≡C−), isothiocyanato azido (—N=N+=N−), formyl (—(CO)—H), thioformyl (—(CS)—H), amino (—NH$_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_5$-$C_{20}$ arylamido (—NH—(CO)-aryl), imino (—CR=NH where R=hydrogen, $C_1$-$C_{24}$ alkyl, $C_5$-$C_{20}$ aryl, $C_6$-$C_{20}$ alkaryl, $C_6$-$C_{20}$ aralkyl, etc.), alkylimino (—CR=N(alkyl), where R=hydrogen, alkyl, aryl, alkaryl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O−), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O−)$_2$), phosphinato (—P(O)(O)), phospho (—PO$_2$), phosphino (—PH$_2$), mono- and di-($C_1$-$C_{24}$ alkyl)-substituted phosphino, mono- and di-($C_5$-$C_{20}$ aryl)-substituted phosphino; and the hydrocarbyl moieties such as $C_1$-$C_{24}$ alkyl (including $C_1$-$C_{18}$ alkyl, further including $C_1$-$C_{12}$ alkyl, and further including $C_1$-$C_6$ alkyl), $C_2$-$C_{24}$ alkenyl (including $C_2$-$C_{18}$ alkenyl, further including $C_2$-$C_{12}$ alkenyl, and further including $C_2$-$C_6$ alkenyl), $C_2$-$C_{24}$ alkynyl (including $C_2$-$C_{18}$ alkynyl, further including $C_2$-$C_{12}$ alkynyl, and further including $C_2$-$C_6$ alkynyl), $C_5$-$C_{30}$ aryl (including $C_5$-$C_{20}$ aryl, and further including $C_5$-$C_{12}$ aryl), and $C_6$-$C_{30}$ aralkyl (including $C_6$-$C_{20}$ aralkyl, and further including $C_6$-$C_{12}$ aralkyl). In addition, the aforementioned functional groups may, if a particular group permits, be further substituted with one or more additional functional groups or with one or more hydrocarbyl moieties such as those specifically enumerated above. For example, the alkyl or alkenyl group may be branched. For example, the "substituent" is an alkyl group, e.g., a methyl group.

As used herein, the term "fragrance composition" means a mixture of fragrance ingredients, e.g., including the polyether compounds of Method 1, et seq., and Method 2, et seq., including auxiliary substances if desired, dissolved in a suitable solvent or mixed with a powdery substrate used to provide a desired odor to a product.

The polyether compounds of Copolymer 1, et seq., Method 1, et seq., and Method 2, et seq. may be used with e.g., with: perfumes, soaps, insect repellants and insecticides, detergents, household cleaning agents, air fresheners, room sprays, pomanders, candles, cosmetics, toilet waters, pre- and aftershave lotions, talcum powders, hair-care products, body deodorants, anti-perspirants, shampoo, cologne, shower gel, hair spray, and pet litter.

Fragrance and ingredients and mixtures of fragrance ingredients that may be used in combination with the disclosed compound for the manufacture of fragrance compositions include, but are not limited to, natural products including extracts, animal products and essential oils, absolutes, resinoids, resins, and concretes, and synthetic fragrance materials which include, but are not limited to, alcohols, aldehydes, ketones, ethers, acids, esters, acetals, phenols, ethers, lactones, furansketals, nitriles, acids, and hydrocarbons, including both saturated and unsaturated compounds and aliphatic carbocyclic and heterocyclic compounds, and animal products.

As used herein, "citronellol polymer" and "prenol polymer" is meant to include all derivatives and cyclic forms of the citronellol and prenol and polymer.

In the present specification, the structural formula of the compounds represents a certain isomer for convenience in some cases, but the present invention includes all isomers, such as geometrical isomers, optical isomers based on an asymmetrical carbon, stereoisomers, tautomers, and the like. In addition, a crystal polymorphism may be present for the compounds represented by the formula, it is noted that any crystal form, crystal form mixture, or anhydride or hydrate thereof is included in the scope of the present invention.

The obtained product is found to have the following physical properties:
Density (g/ml): 0.915
Refractive Index (@20 C): 1.465
Surface Tension (cP @21 C): 598

Analysis of the product by $^1$H-NMR permits characterization of the degree of alcohol incorporation and/or olefin etherification. The diagnostic ether methylene peaks shift to the 3.0-3.5 ppm range in CDCl3 solvent, compared to the corresponding alcoholic methylene peaks at 3.5-4.0 ppm. The diagnostic methyl peaks associated with the dimethyl ether motif of the citronellol monomer and of the polymer product appear in the 1.0-1.5 ppm range.

FIG. 1 shows the $^1$H NMR spectrum for the purified product. The spectrum is consistent with a copolymer system that is predominantly capped by OH groups, as evidenced by the very diminished isoprenyl moiety present (both the olefin protons and the corresponding isoprenyl methyl protons), and the predominant presence of hydroxymethylene protons between 3.5 and 3.7 ppm. Further, it can be seen that there is significant oligomerization internally with regard to ether linkages that are evidenced by the ether-methylene protons between 3.2 and 3.4 ppm and the corresponding methyl groups adjacent to the ether.

Without being bound by theory, the NMR spectrum is consistent with a copolymer structure such as follows:

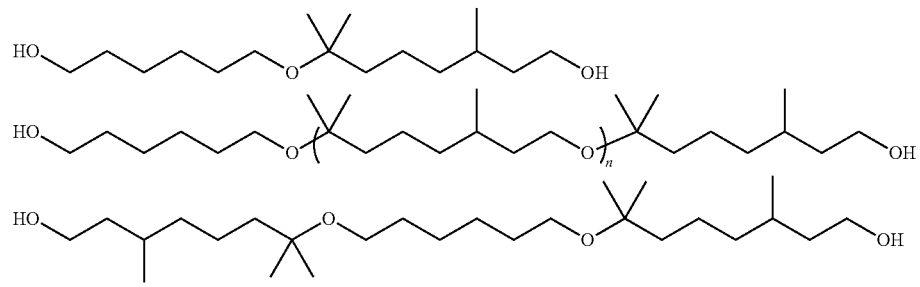

All percentages used herein, unless otherwise indicated, are by volume.

All ratios used herein, unless otherwise indicated, are by molarity.

EXAMPLES

Example 1. Synthesis of Citronellol/1,6-hexanediol Copolymer 500 g of Citronellol and 94.5 g of 1,6-hexanediol (0.25 eq) is mixed thoroughly at 50° C. The mixture is pumped into a 6 ft, ¼ inch tube packed with Amberlyst ion-exchange resin at 2 mL/min flow rate. The reaction proceeds at 50° C. The crude product is collected at the end of the tube and nuclear magnetic resonance spectroscopy (NMR) and gas chromatography (GC) are used to monitor the reaction. After the reaction is deemed complete, the crude product is diluted with hexane and washed with saturated sodium carbonate solution until the pH of the aqueous phase is about 8. The organic phase is then collected, concentrated, and prepared for distillation to remove any monomer. Unreacted monomers are distilled off at pot temperature 83-165° C. at a pressure 0.7-2.85 mBar. The total yield of the reaction is 56.4% of a viscous, water-white, odorless fluid.

The product obtained from this Example is found to be a glossy, shiny film former, which can be used as a solvent and as an emollient. The polymer's physical and chemical properties are similar to the emollient octyldodecanol, suggesting that it could be used as a replacement for octyldodecanol.

Example 2: Synthesis of Other Citronellol CoPolymers

Similar synthetic and analytical procedures as described in Example 1 are used to obtain copolymers derived from the following combinations of monomers: (1) citronellol and linalool; (2) citronellol and geraniol; (3) citronellol and nerol; (4) citronellol and d-limonene; (5) citronellol and glycerol; (6) citronellol and dihydromercene; (7) citronellol and triethylene glycol; (8) citronellol and 1,3-propanediol; (9) citronellol and 1,2-propanediol; (10) citronellol and ethylene glycol. Crude $^1$H NMR spectra for these products, before removal of unreacted monomeric species, are shown in FIG. 2-6.

Figure 2:
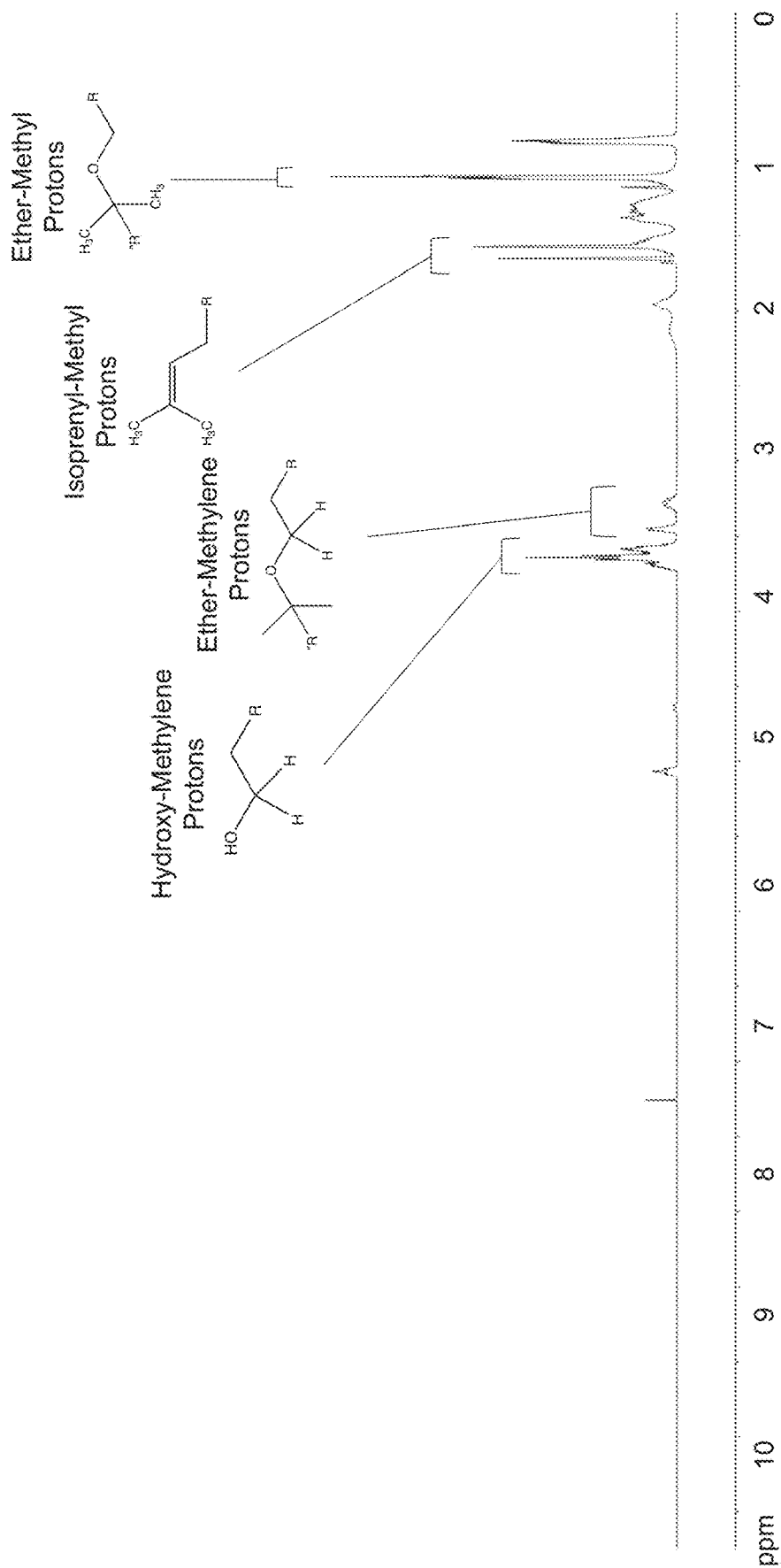
FIG. 2 shows the proton-NMR spectrum obtained according to Example 2 for the crude product obtained from copolymerization of citronellol and triethylene glycol.

FIG. 2: The co-polymerization of citronellol and triethylene glycol yields a crude mixture that has all of the diagnostic peaks for the desired copolymer product. It shows the presence of methyl groups adjacent to the newly formed ether linkage, as well as ether-methylene protons between 3-3.5 ppm, indicating that the desired polymerization has taken place.

Figure 3:
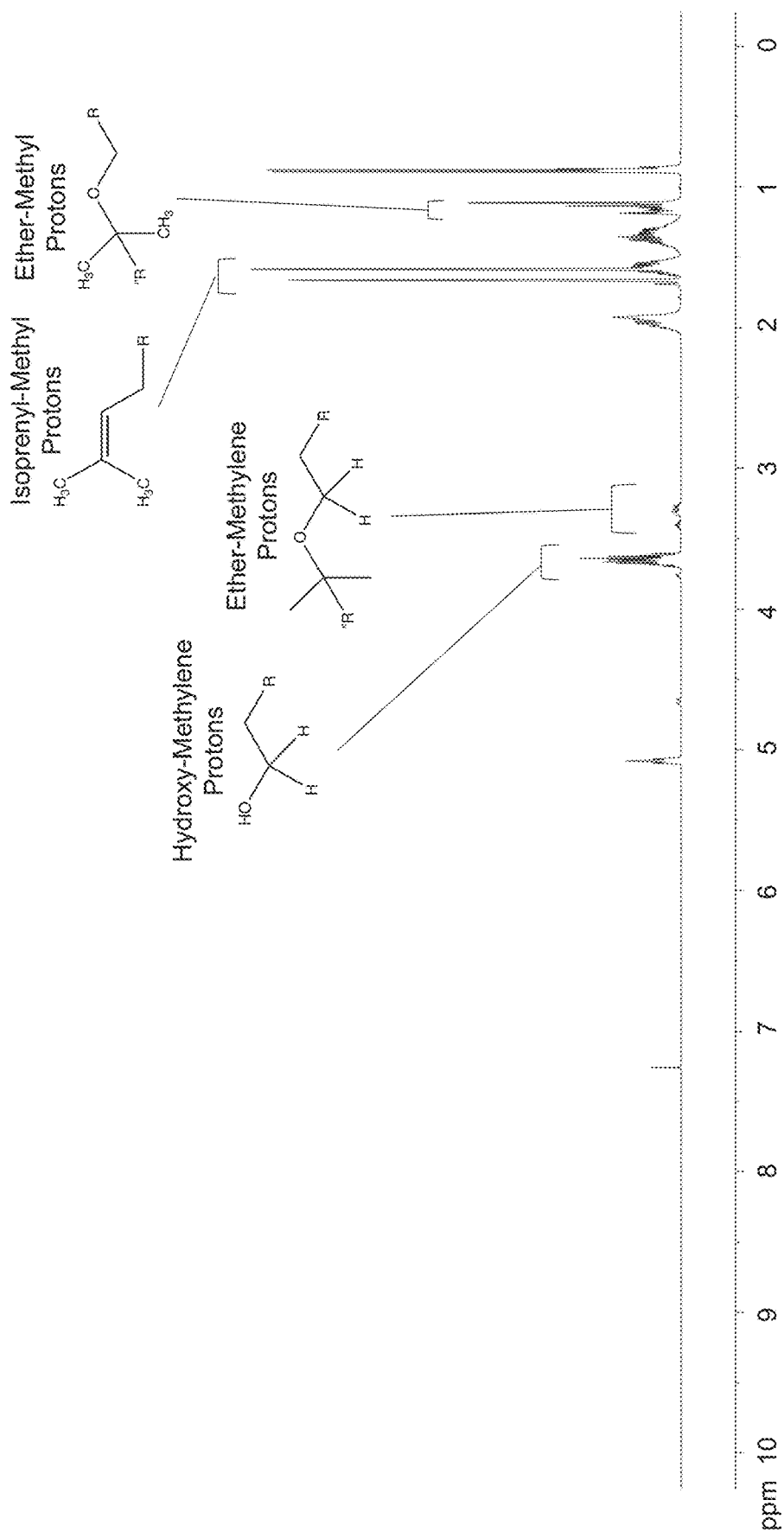
FIG. 3 shows the proton-NMR spectrum obtained according to Example 2 for the crude product obtained from copolymerization of citronellol and glycerol.

FIG. 3: The co-polymerization of citronellol and glycerol yields a crude mixture that has all of the diagnostic peaks for the desired copolymer product. It shows the presence of methyl groups adjacent to the newly formed ether linkage, as well as ether-methylene protons between 3-3.5 ppm, indicating that the desired polymerization has taken place.

Figure 4:
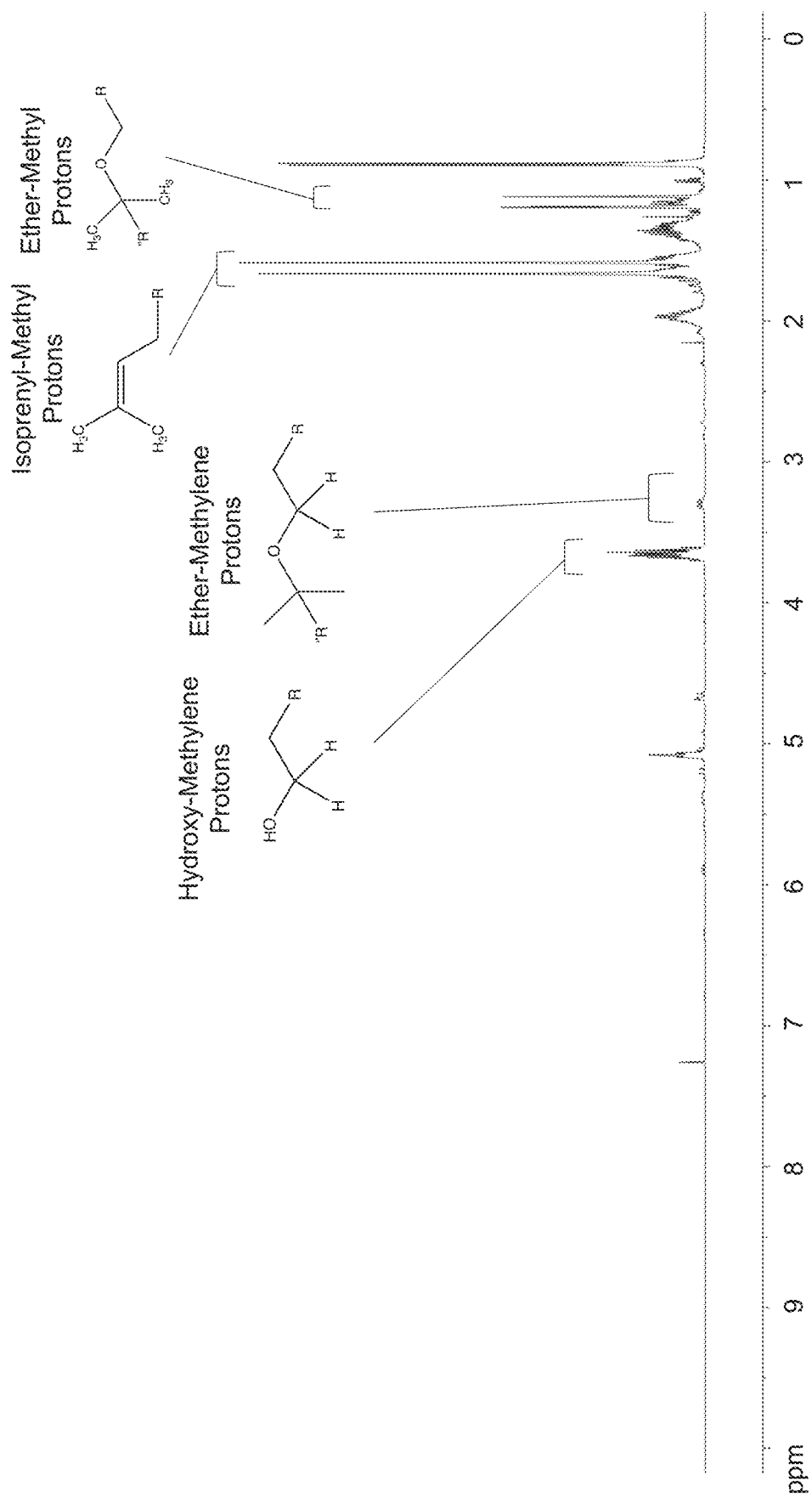
FIG. 4 shows the proton-NMR spectrum obtained according to Example 2 for the crude product obtained from copolymerization of citronellol and linalool.

FIG. 4: The co-polymerization of citronellol and linalool yields a crude mixture that has all of the diagnostic peaks for the desired polymer product. It shows the presence of methyl groups adjacent to the newly formed ether linkage, as well as ether-methylene protons between 3-3.5 ppm, indicating that the desired polymerization has taken place.

Figure 5:
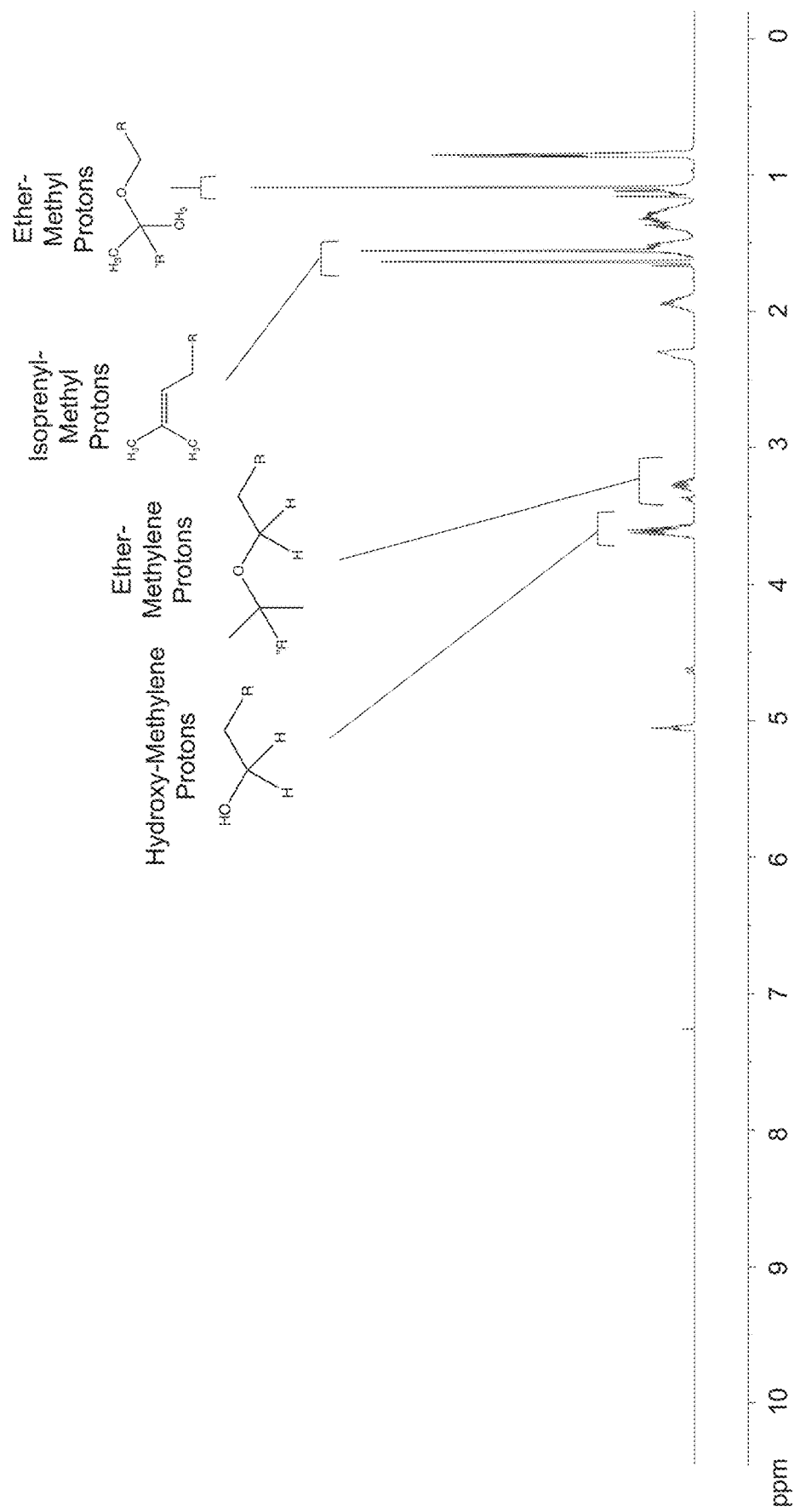
FIG. 5 shows the proton-NMR spectrum obtained according to Example 2 for the crude product obtained from copolymerization of citronellol and ethylene glycol.

FIG. 5: The co-polymerization of citronellol and ethylene glycol yields a crude mixture that has all of the diagnostic peaks for the desired polymer product. It shows the presence of methyl groups adjacent to the newly formed ether linkage, as well as ether-methylene protons between 3-3.5 ppm, indicating that the desired polymerization has taken place.

Figure 6:
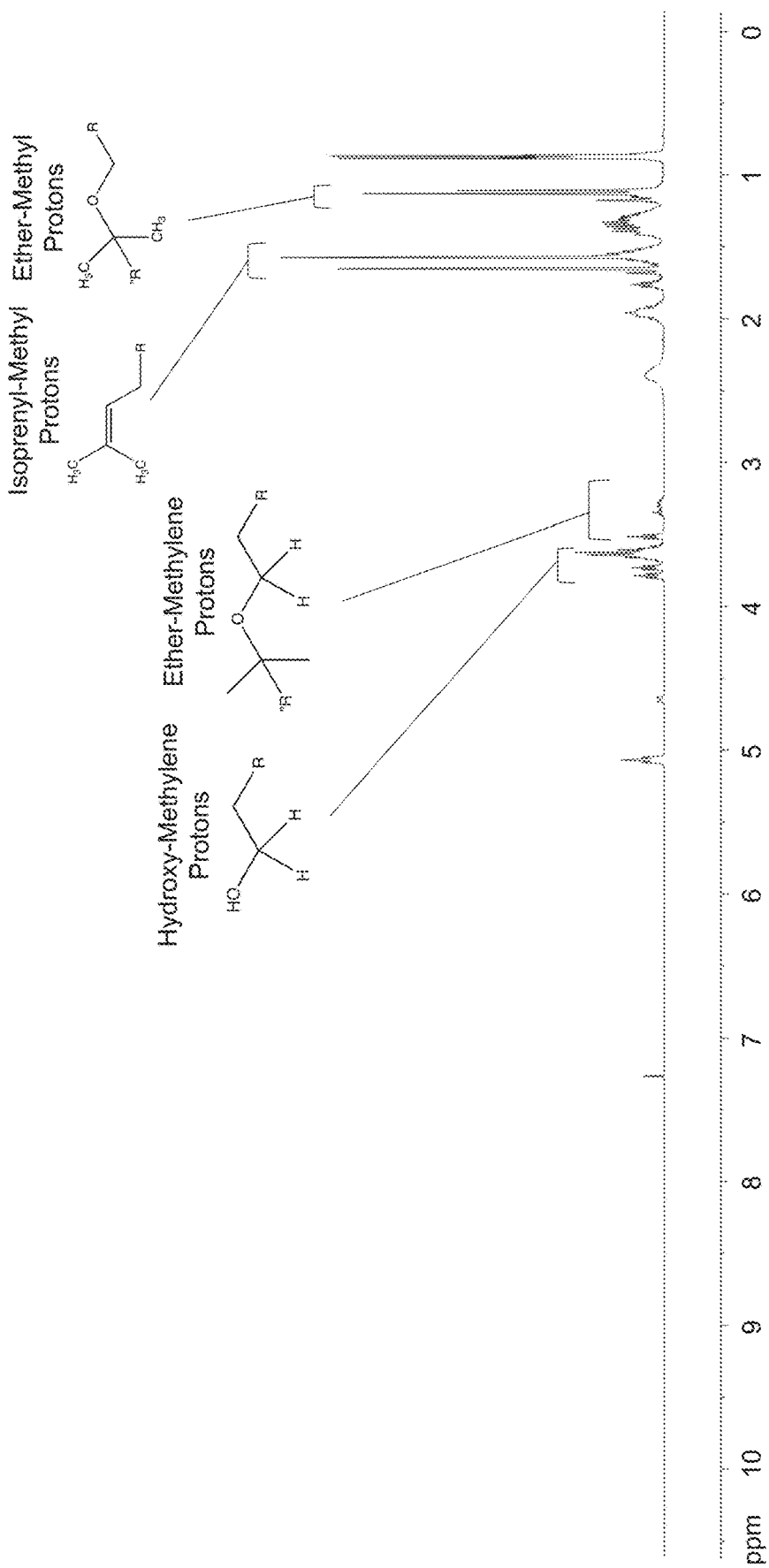
FIG. 6 shows the proton-NMR spectrum obtained according to Example 2 for the crude product obtained from copolymerization of citronellol and 1,3-propanediol.

FIG. 6: The co-polymerization of citronellol and triethylene glycol yields a crude mixture that has all of the diagnostic peaks for the desired polymer product. It shows the presence of methyl groups adjacent to the newly formed ether linkage, as well as ether-methylene protons between 3-3.5 ppm, indicating that the desired polymerization has taken place.

The reactions conditions may be modified to adjust the molar ratio of monomers and/or to incorporate more than to distinct monomers to arrive at a variety of different copolymer products.

Example 3: Cosmetic Skin Formulation

The citronellol/1,6-hexanediol copolymer obtained from Example 1 is used to prepare a cosmetic skin formulation as shown in the table below.

| Purpose | Ingredients | % (by weight) |
| --- | --- | --- |
| Emollient | Triglyceride Blend | 15 |
| Emollient | Triglyceride | 15 |
| Non-gelling thickener/co-emulsifier | Cetyl Alcohol | 5 |
| Non-gelling thickener | Cetearyl Alcohol | 7 |
| Non-gelling thickener | Magnesium Stearate | 5 |
| Film former/emollient | Product of EXAMPLE 1 | 50 |
| Pigment | Titanium Oxide | 1-2 |
| Pigment | Iron Oxide, Red | 0.20-0.50 |
| Preservative | Vitamin E | 0.3 |
| Fragrance | Fragrance | QS |

The skin formulation is prepared according to the following procedure:
(A) The copolymer of Example 1 is combined with the triglyceride blend, triglyceride, cetyl alcohol, stearyl alcohol and magnesium stearate in a 150 mL glass beaker.
(B) The beaker is heated on a hot plate at 70-75° C. (+/−5° C.) with continuous stirring.
(C) The titanium dioxide and iron oxide are ground together to form a powder using a mortar and pestle, in a ratio as needed to obtain the desired color.
(D) The pigment powder of Step (C) is added to the mixture from Step (B) and stirred until homogenous.

(E) The stirring mixture is cooled to about 30-40° C., and then the vitamin E and fragrance are added, followed by gentle mixing.
(F) The mixture is poured mixture into a round 15 ml glass container and stored in refrigerator at about 4° C. to cool.

The formulation obtained is a homogenous dark pink semisolid with a pH between 5.0 and 5.5. It can be applied smoothly to the skin with a glossy, shiny effect. It does not result in over-drying of the skin.

This formulation is found to be safe and effective as a lip and cheek stain.

The invention claimed is:

1. A copolymer formed from a combination of monomeric units, wherein the monomeric units consist of units X and units Y, wherein the unit X has the formula:

and wherein the unit Y has a formula selected from Y1, Y2, Y3 and Y4:

wherein $R^1$ is 3-methylpentyl, linear hexyl, 3-methyl-2-pentylene, or 3-methyl-3-vinylpropyl, $R^2$ is ethyl, linear propyl, isopropyl, linear hexyl, linear nonanyl, a polyethoxy of the formula $(OCH_2CH_2)_n$ wherein n is 3, or 2-hydroxypropyl, $R^3$ is ethyl, linear propyl, linear hexyl, or linear heptyl, and $R^4$ is ethyl; and provided that when the copolymer comprises only groups X and groups Y1 then substituent R1 of group Y1 is not 3-methylpentyl;

and wherein the copolymer is terminated with at least one terminal unit Z selected from Z, Z1, Z2, Z3, Z4 and Z5:

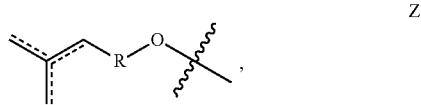

-continued

Z1
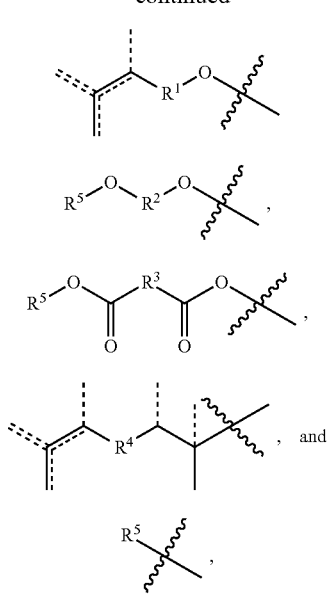

Z2

Z3

Z4

Z5 wherein the substituent group R of terminal unit Z is 3-methylpentyl, and the substituent groups $R^1$, $R^2$, $R^3$ and/or $R^4$ of the terminal units Z1, Z2, Z3, and/or Z4, as applicable, is/are the same as said groups of the corresponding units Y1, Y2, Y3 and/or Y4 of the copolymer, and wherein $R^5$ is selected from H, OH, $C_{1-20}$alkyl, aryl, aryl$C_{1-2}$ alkyl, $OC_{1-20}$alkyl, or $OC_{1-12}$ alkyl), O-aryl, O-aryl$C_{1-2}$ alkyl, C(O)—$C_{1-20}$ alkyl, OC(O)—$C_{1-20}$ alkyl, C(O)-aryl, and O—C(O)-aryl;

wherein - - - - - represents an optional methyl group; and wherein, ===== represents a single bond or double bond.

2. The copolymer according to claim 1, wherein the monomeric unit Y is Y1.

3. The copolymer according to claim 1, wherein the monomeric unit Y is Y2.

4. The copolymer according to claim 1, wherein any one or more of $R^1$, $R^2$, $R^3$, and $R^4$, is optionally substituted linear $C_1$-$C_{12}$ alkyl or optionally substituted branched $C_1$-$C_{12}$ alkyl.

5. The copolymer according to claim 4, wherein any one or more of $R^1$, $R^2$, $R^3$, and $R^4$, is 3-methylpentyl, linear hexyl, linear nonanyl, linear propyl, or ethyl.

6. The copolymer according to claim 1, wherein any one or more of $R^1$, $R^2$, $R^3$, and $R^4$, is $C_{2-12}$ alkenyl, optionally $C_{2-12}$ alkenyl having from 1 to 4 double bonds.

7. The copolymer according to claim 4, wherein one or more of $R^1$, $R^2$, $R^3$, and $R^4$, is 3-methyl-2-pentylene or 3-methyl-3-vinylpropyl.

8. The copolymer according to claim 1, wherein the one or more monomeric units Y are selected from:

a. Y1 wherein $R^1$ is

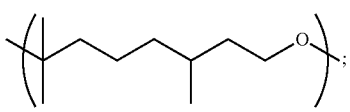

b. Y1 wherein $R^1$ is

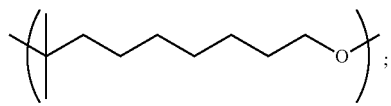

c. Y1 wherein $R^1$ is

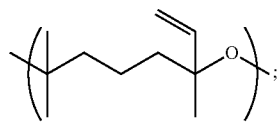

d. Y1 wherein $R^1$ is

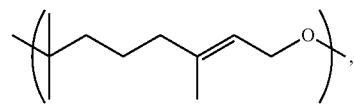

wherein Y1 is

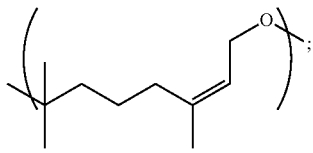

e. Y2 wherein $R^2$ is ethyl;
f. Y2 wherein $R^2$ is linear propyl;
g. Y2 wherein $R^2$ is isopropyl;
h. Y2 wherein $R^2$ is linear hexyl;
i. Y2 wherein $R^2$ is linear nonanyl;
j. Y2 wherein $R^2$ is a polyethoxy of the formula $(OCH_2CH_2)n$ wherein n is 3;
k. Y2 wherein $R^2$ is 2-hydroxypropyl;
l. Y3 wherein $R^3$ is ethyl;
m. Y3 wherein $R^3$ is linear propyl;
n. Y3 wherein $R^3$ is linear hexyl;
o. Y3 wherein $R^3$ is linear heptyl;
p. Y4 wherein $R^4$ is

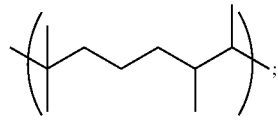

q. Y4 wherein $R^4$ is

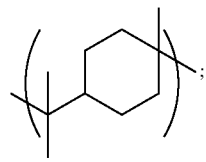

or combinations thereof.

9. The copolymer according to claim 1, wherein the copolymer consists of monomeric units X which

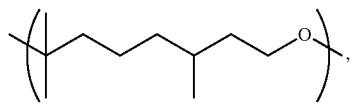

are
in combination with monomeric units Y selected from:
a. Y2 wherein $R^2$ is ethyl;
b. Y2 wherein $R^2$ is linear propyl;
c. Y2 wherein $R^2$ is linear nonanyl; and
d. Y2 wherein $R^2$ is linear hexyl;
or combinations thereof.

10. The copolymer according to claim 1, wherein the copolymer is a linear polymer comprising from 1 to 20 units X and from 1 to 20 units Y in any order, optionally wherein all of the 1 to 20 units X are the same, and further optionally wherein all of the 1 to 20 units Y are the same.

11. The copolymer according to claim 10, wherein the X units and Y units are organized in block formation and wherein the polymer comprises a sequence of monomeric units $(X)n(Y)m$, wherein n and m are each an integer from 1 to 20.

12. The copolymer according to claim 1, wherein the copolymer is terminated with at least one terminal unit Z:

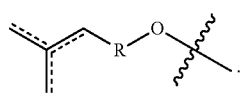

13. The copolymer according claim 1, wherein the copolymer has the Formula Y:

A—[(X)n(Y)m]—B wherein A and B are each independently a terminal group selected from Z, Z1, Z2, Z3, Z4 and Z5, and wherein n and m are each independently an integer from 1 to 20, and wherein the n units X and the m units Y are arranged in a linear sequence in any order.

14. A fragrance, perfume, soap, insect repellent, insecticide, detergent, household cleaning agent, air freshener, room spray, pomander, candle, cosmetic, toilet water, pre- and/or after-shave lotion, talcum powder, haircare product, body deodorant, anti-perspirant, shampoo, pet litter, topical skin care, paint or coating, lubricant, plastic, defoamer, hydraulic fluid, antimicrobial, crop care, or enhanced oil recovery composition, a solution or suspension comprising the copolymer of claim 2, dissolved or suspended in a solvent or mixture of solvents.

15. The composition according to claim 14, which is a fragrance, perfume, soap, insect repellent, insecticide, candle, cosmetic, or lubricant composition.

16. A method of making the copolymer according to claim 1, or a salt thereof, wherein the method comprises the steps of (1) introducing into a reactor a compound of Formula A:

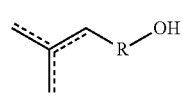

and at least one of a compound of Formula A1, A2, A3 or A4,

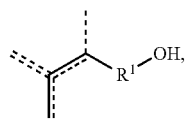

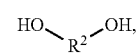

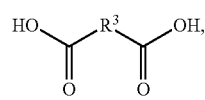

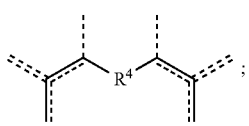

wherein, each of R, $R^1$, $R^2$, $R^3$, $R^4$ and/or is optionally substituted $C_1$-$C_{12}$ alkyl, $C_2$-$C_{12}$ alkenyl, or polyethoxy;

and (2) exposing said compound to a solid ion-exchange resin, thereby causing the copolymerization of the compound of Formula A with the compound of Formula A1, A2, A3 and/or A4, to yield the copolymer, wherein if $R^5$ is present then $R^5$ is H;

and (3) isolating and/or purifying the copolymer.

17. The method according to claim 16, wherein the solid exchange resin is a resin-bound acid catalyst.

18. The copolymer according to claim 1, wherein the unit Y has the formula Y2:

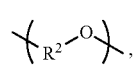

wherein $R^2$ is ethyl, linear propyl, isopropyl, linear hexyl, linear nonanyl, or 2-hydroxypropyl, and wherein the copolymer is terminated with at least one terminal unit Z

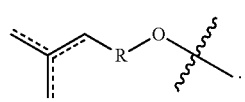

19. The copolymer according to claim 18, wherein $R^2$ is ethyl, linear propyl, isopropyl, or linear hexyl.

20. The copolymer according to claim 1, wherein the unit Y has the formula Y3:

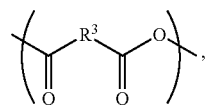

wherein $R^3$ is ethyl, linear propyl, isopropyl, linear hexyl, or linear heptyl, and wherein the copolymer is terminated with at least one terminal unit Z

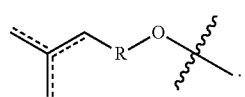
21. The copolymer according to claim 20, wherein $R^3$ is ethyl, linear propyl, isopropyl, or linear hexyl.
* * * * *

UNITED STATES PATENT AND TRADEMARK OFFICE
CERTIFICATE OF CORRECTION

PATENT NO. : 12,084,543 B2
APPLICATION NO. : 16/978076
DATED : September 10, 2024
INVENTOR(S) : Patrick Foley et al.

It is certified that error appears in the above-identified patent and that said Letters Patent is hereby corrected as shown below:

In the Specification

Column 6, Line 65, "R, $R^2$, $R^3$, and $R^4$," should be changed to "R, $R^1$, $R^2$, $R^3$, and $R^4$,"

Column 7, Line 15, "R, $R^2$, $R^3$, and $R^4$," should be changed to "R, $R^1$, $R^2$, $R^3$, and $R^4$,"

Column 7, Line 19, "R, $R^2$, $R^3$, and $R^4$," should be changed to "R, $R^1$, $R^2$, $R^3$, and $R^4$,"

Column 7, Line 25, "R, $R^2$, $R^3$, and $R^4$," should be changed to "R, $R^1$, $R^2$, $R^3$, and $R^4$,"

Column 7, Line 28, "R, $R^2$, $R^3$, and $R^4$," should be changed to "R, $R^1$, $R^2$, $R^3$, and $R^4$,"

Column 7, Line 31, "R, $R^2$, $R^3$, and $R^4$," should be changed to "R, $R^1$, $R^2$, $R^3$, and $R^4$,"

In the Claims

Claim 1, Column 30, Line 18 to 26, the structure of formula X,

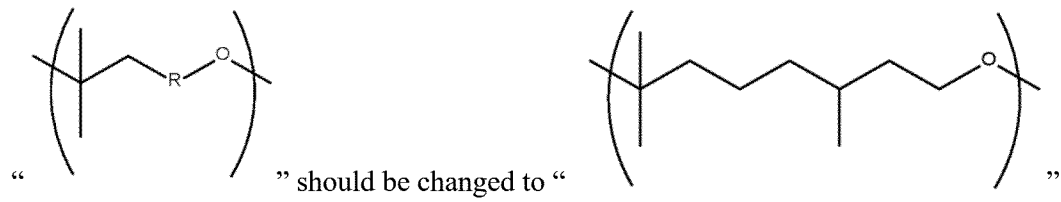

Claim 7, Column 31, Line 53, "according to claim 4" should be changed to "according to claim 6"

Claim 8, Column 32, Line 24, "wherein Y1 is" should be changed to "or wherein Y1 is"

Claim 16, Column 34, Line 21, "$R^3$, $R^4$, and/or" should be changed to "$R^3$ and/or $R^4$,"

Signed and Sealed this
Eleventh Day of February, 2025

Coke Morgan Stewart
*Acting Director of the United States Patent and Trademark Office*